(12) United States Patent
Schneider et al.

(10) Patent No.: US 7,361,502 B2
(45) Date of Patent: Apr. 22, 2008

(54) NUCLEIC ACID MOLECULE ENCODING A NEURONAL SERINE-THREONINE PROTEIN KINASE

(75) Inventors: Armin Schneider, Heidelberg (DE);
Bettina Klaussner, Auckland (NZ);
Achim Fischer, Heidelberg (DE);
Dieter Newrzella, Dossenheim (DE);
Bernhard Götz, Heidelberg (DE);
Moritz Rossner, Schwetzingen (DE);
Gisela Eisenhardt, Heidelberg (DE);
Rohini Kuner, Heidelberg (DE);
Annette Trutzel, Frankenthal (DE);
Birgitta Kammandel, Heidelberg (DE);
Stephanie Jomana Naim, Heidelberg (DE); Markus Schwaninger, Heidelberg (DE)

(73) Assignee: SYGNIS Bioscience GmbH & Co. KG, Heidelberg (DE)

( * ) Notice: Subject to any disclaimer, the term of this patent is extended or adjusted under 35 U.S.C. 154(b) by 336 days.

(21) Appl. No.: 10/276,645

(22) PCT Filed: May 17, 2001

(86) PCT No.: PCT/EP01/05660

§ 371 (c)(1),
(2), (4) Date: Jun. 4, 2003

(87) PCT Pub. No.: WO01/88108

PCT Pub. Date: Nov. 22, 2001

(65) Prior Publication Data

US 2004/0087784 A1 May 6, 2004

(30) Foreign Application Priority Data

May 17, 2000 (DE) .............................. 100 24 171

(51) Int. Cl.
*C12N 15/00* (2006.01)
*C12N 7/01* (2006.01)
*C07H 21/04* (2006.01)
*C07K 14/435* (2006.01)

(52) U.S. Cl. .................. 435/320.1; 536/23.2; 530/350; 435/235.1

(58) Field of Classification Search ...................... None
See application file for complete search history.

(56) References Cited

U.S. PATENT DOCUMENTS 5,863,729 A * 1/1999 Piwnica-Worms ............. 435/6
2004/0018185 A1* 1/2004 Yue et al. ................... 424/94.5

FOREIGN PATENT DOCUMENTS

WO    WO 94/01582      * 1/1994
WO    WO 97 23625 A    7/1997
WO    WO 98 01756      1/1998
WO    WO 99 42592 A    8/1999

OTHER PUBLICATIONS

Kato et al. Isolation of a novel human gene, MARKL1, homologous to MARK3 and its involvement in hepatocellular carcinogenesis. Neoplasia 3(1): 4-9, 2001.*
Schneider et al. Identification of regulated genes during permanent focal cerebral ischaemia: characterization of the protein kinase 9b5/MARKL1/MARK4. J. Neurochem 88: 1114-1126, 2004.*
Force et al. Inhibitors of protein kinase signaliing pathways. Circulation 109: 1196-1205, 2004.*
Beghini et al. The neural progenitor-restricted isoform of the MARK4 gene in 19q13.2 in upregulated in human gliomas and overexpressed in a subset of glioblastoma cell lines. Oncogene 22(17):2581-2591, 2003.*
Trinczek et al. MARK4 is a novel microtubule-associated proteins/microtubule affinity-regulating kinase that binds to the cellular microtubule network and to centrosomes. J Biol Chem 279(7): 5915-5923, 2004.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res. 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
GenBank data base accession No. AB049127, Kato et al. Apr. 10, 2001.
GenBank data base accession No. AB058763, Nagase et al. Jun. 8, 2001.
GenBank database accession No. AC005781.1, Lamerdin et al. Oct. 8, 1998.
GenBank data base accession No. AF240782, Darmon et al. Apr. 20, 2000.
GenBank data base accession No. AK027619, Takao et al. May 15, 2001.

(Continued)

*Primary Examiner*—Bridget E Bunner
(74) *Attorney, Agent, or Firm*—Needle & Rosenberg, PC

(57) ABSTRACT

The present invention relates to a gene and the coded protein thereof that is involved in the development of sequelae of local ischaemia. The new protein is a serine threonine protein kinase and provides a new therapeutic approach to the prophylaxis and therapy of apoplexy.

5 Claims, 8 Drawing Sheets

OTHER PUBLICATIONS

GenBank data base accession No. U64205, Peng et al. Apr. 28, 1998.

Drewes et al. MARK, a novel family of protein kinases that phosphorylate microtubule-associated proteins and trigger microtubule disruption *Cell, Cell Press, Cambridge, NA*, US, 89:297-308 (Apr. 18, 1997).

GenBank database accession No. AAF64455.1, Darmon et al., Apr. 19, 2000.

GenBank database accession No. AF177024.1, Lee et al., May 3, 2000.

GenBank database accession No. X70764.1 Inglis et al., Apr. 18, 2005.

* cited by examiner

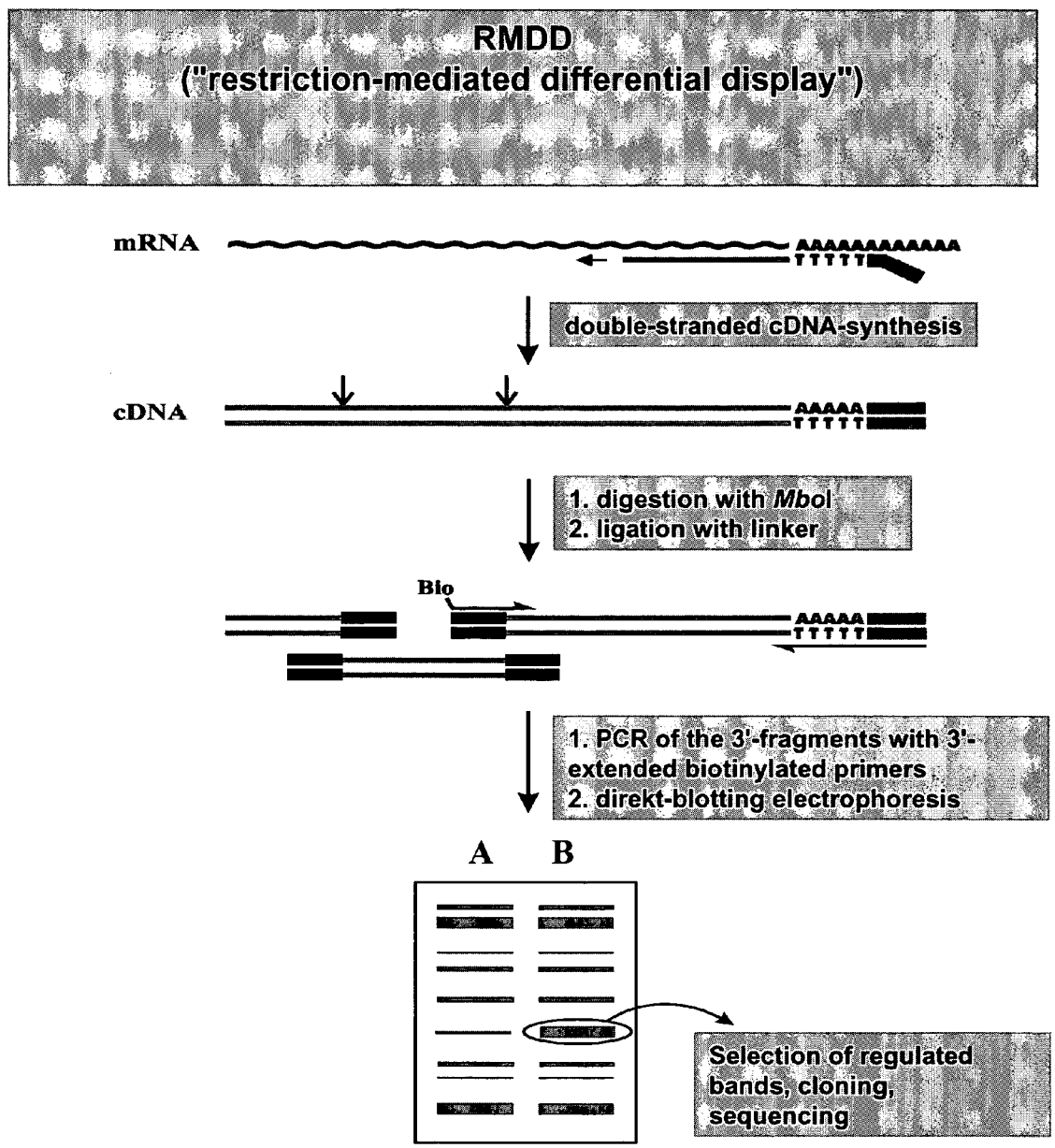
Figure 1: Principle of the RMDD-method

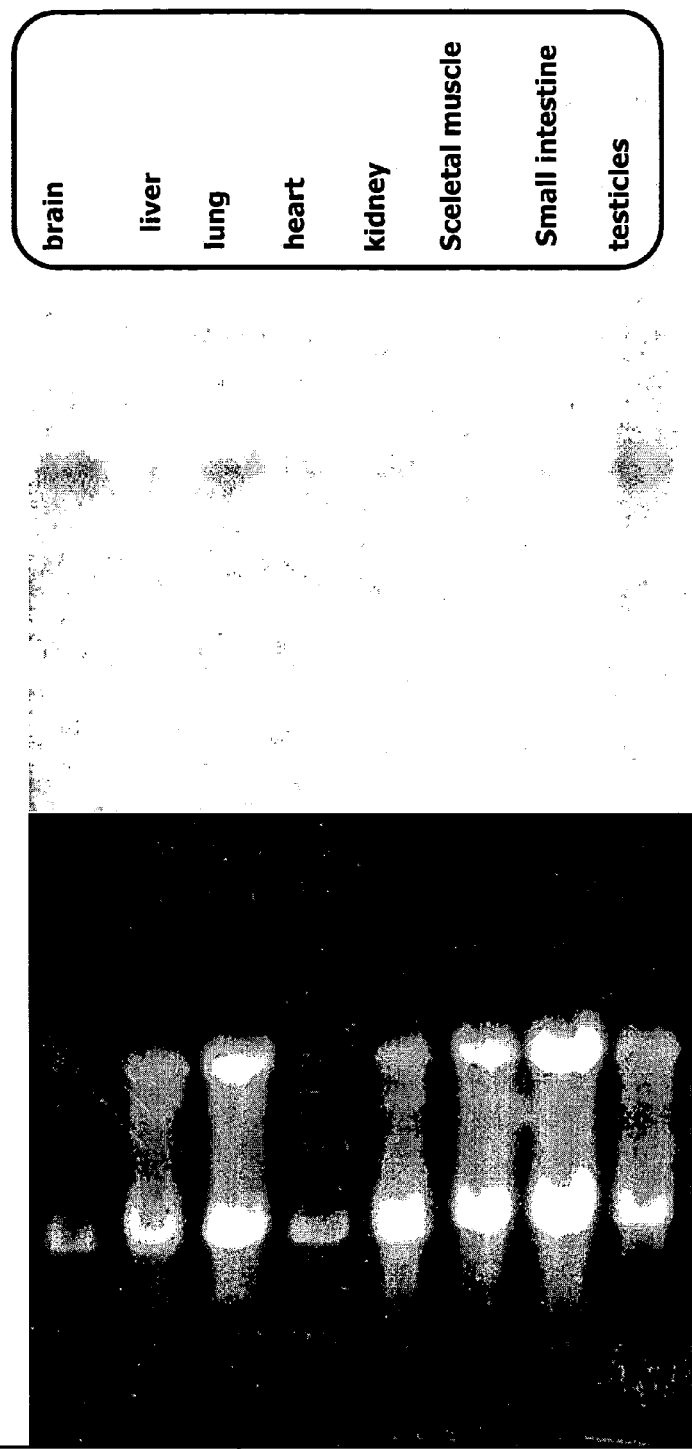
Figure 2: Tissue distribution of 9B5 in the rat

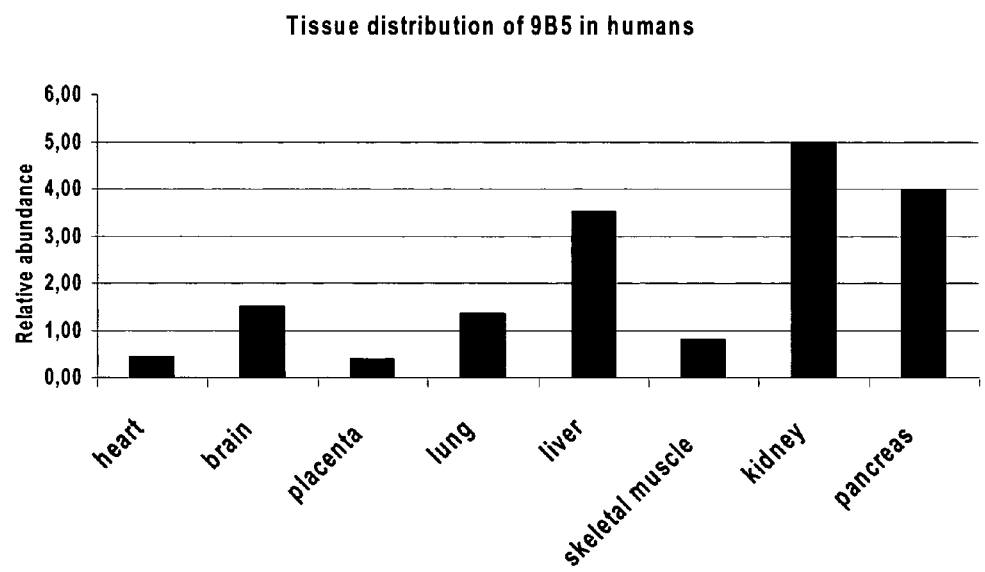
Figure 3: Tissue distribution of 9B5 in humans

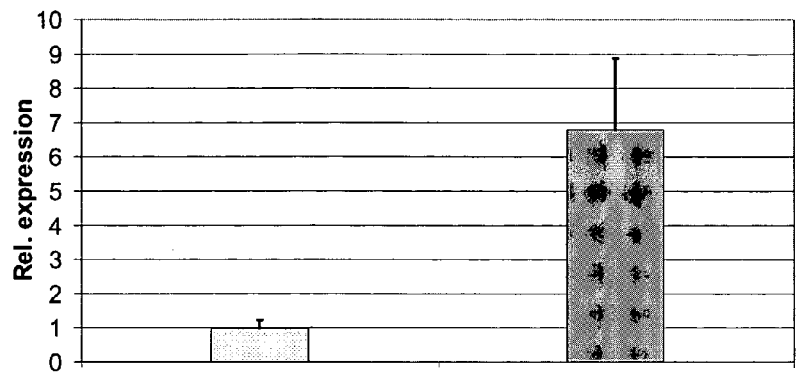
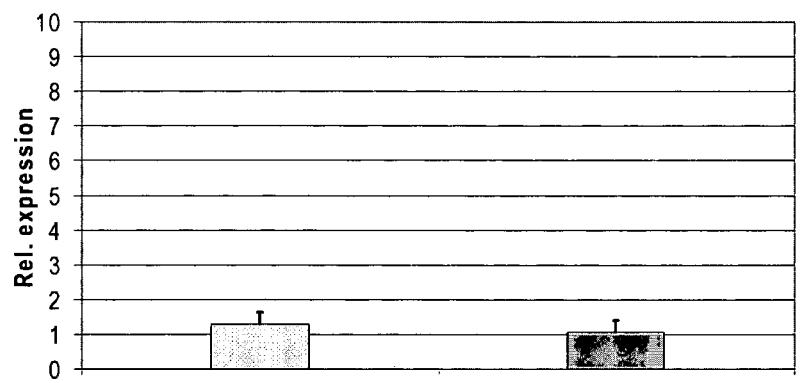
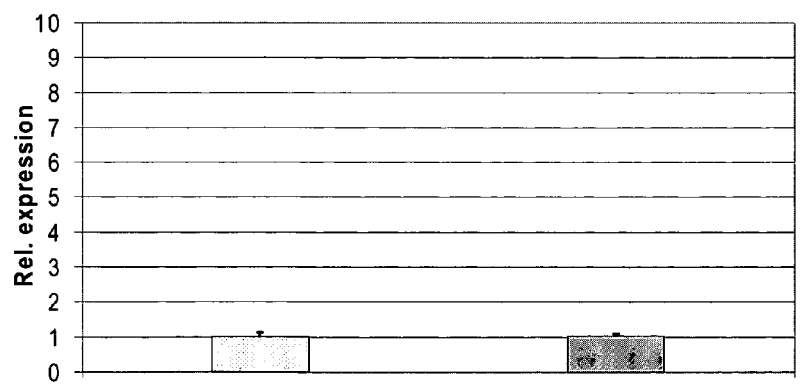
Figure 4: Induktion of 9B5 by focal cerebral ischaemia

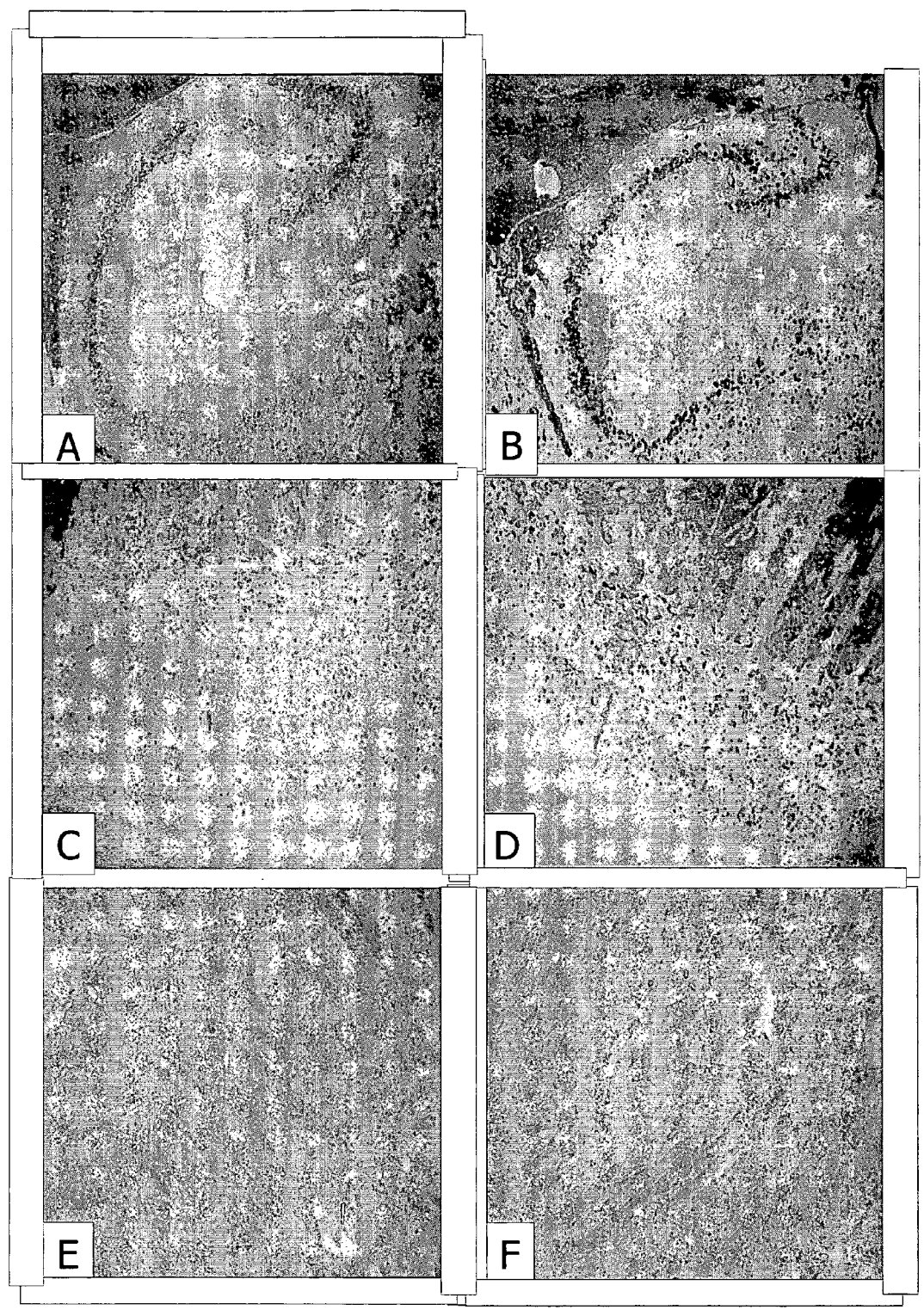
Figure 5: *In situ* hybridisation of murine brains after focal ischaemia
A, B hippocampus, each contralaterally vs. ischaemic side; C,D cortex; E,F thalamus.

MSSRTVLAPGNDRNSDTHGTLGSGRSSDKGPSWSSRSLGARCRNSIASCPEEQPHVGN

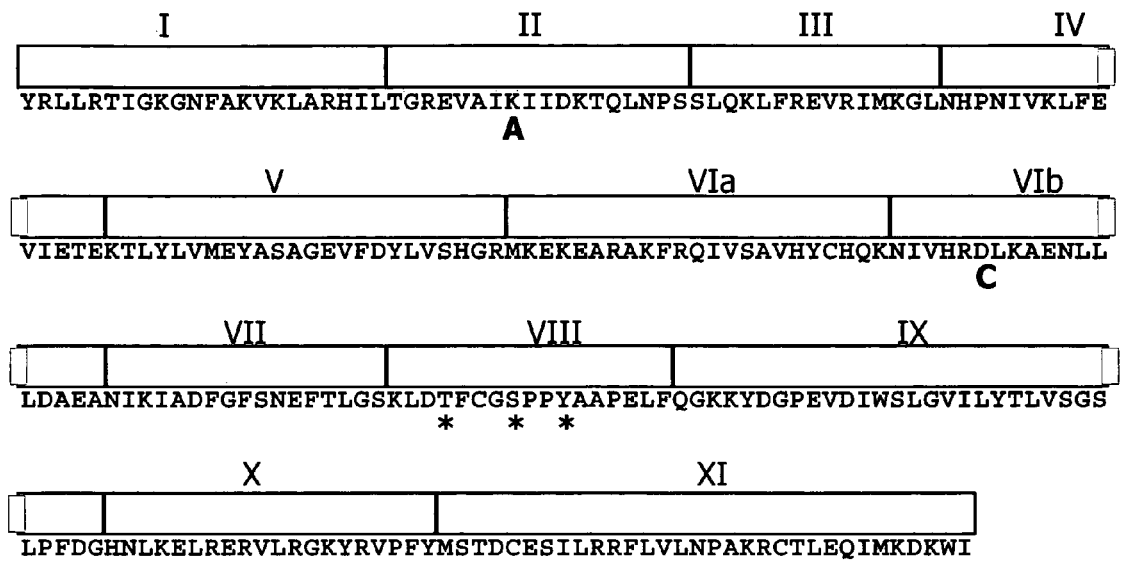

YRLLRTIGKGNFAKVKLARHILTGREVAIKIIDKTQLNPSSLQKLFREVRIMKGLNHPNIVKLFE

VIETEKTLYLVMEYASAGEVFDYLVSHGRMKEKEARAKFRQIVSAVHYCHQKNIVHRDLKAENLL

LDAEANIKIADFGFSNEFTLGSKLDTFCGSPPYAAPELFQGKKYDGPEVDIWSLGVILYTLVSGS

LPFDGHNLKELRERVLRGKYRVPFYMSTDCESILRRFLVLNPAKRCTLEQIMKDKWI

NIGYEGEELKPYTEPEEDFGDTKRIEVMVGMGYTREEIKESLTSQKYNEVTATYLLLGRKTEEGG
DRGAPGLALARVRAPSDTTNGTSSSKGTSHSKGQRSSSSTYHRQRRHSDFCGPSPAPLHPKRSPT
STGEAELKEERLPGRKASCSTAGSGSRGLPPSSPMVSSAHNPNKAEIPERRKDSTSTPNNLPPSM
MTRRNTYVCTERPGAERPSLLPNGKENSSGTPRVPPASPSSHSLAPPSGERSRLARGSTIRSTFH
GGQVRDRRAGGGGGGVQNGPPASPTLAHEAAPLPAGRPRPTTNLFTKLTSKLTRRVADEPERIG
GPEVTSCHLPWDQTETAPRLLRFPWSVKLTSSRPPEALMAALRQATAAARCRCRQPQPFLLACLH
GGAGGPEPLSHFEVEVCQLPRPGLRGVLFRRVAGTALAFRTLVTRISNDLEL

Figure 6: catalytic region of 9B5
I= phosphat anchor, VIb = catalytic region, VII-VIII = activation loop, I-XI = subdomains of the catalytic region (after Hanks and Hunter, 1995), * = activation sites, A= ATP-binding site, C= active center.

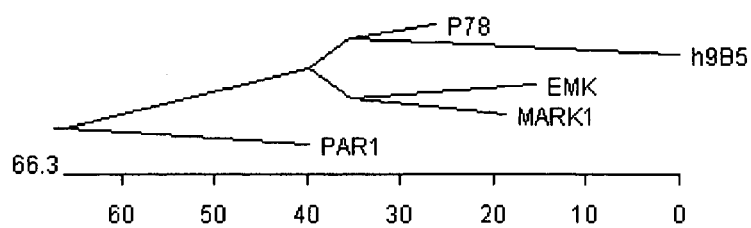
Figure 7: Phylogenetic tree of the homologues
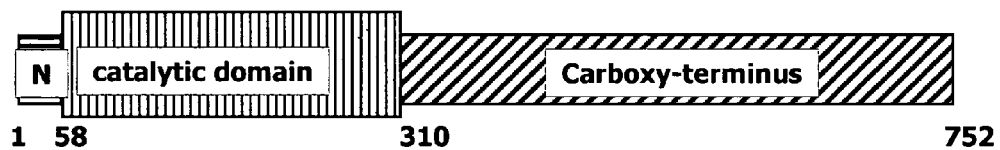
Figure 8: domain structure of 9B5
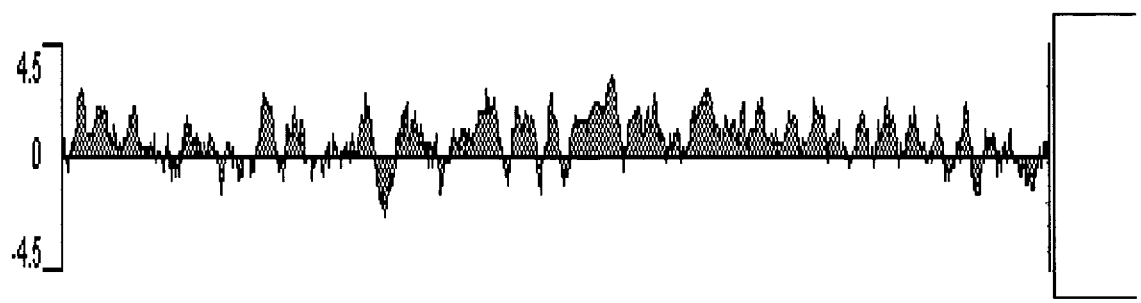
Figure 9: Hydrophobicity after Kyte-Doolittle

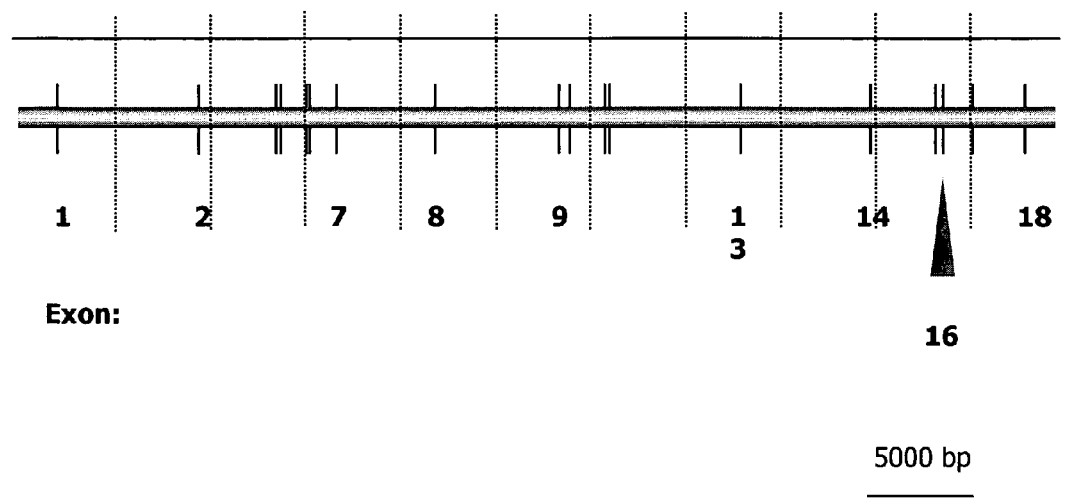
Figure 10: Genomic structure of 9B5 in humans.

NUCLEIC ACID MOLECULE ENCODING A NEURONAL SERINE-THREONINE PROTEIN KINASE

The present application is a 35 U.S.C. §371 national phase application from, and claims priority to, international application PCT/EP01/05660, filed May 17, 2001 (published under PCT Article 21(2) in English), which claims priority to German patent application Ser. No. 100 24 171.9, filed May 17, 2000, which applications are incorporated herein in their entirety by this reference.

The present invention relates to a serine threonine protein kinase, nucleic acids that code this kinase and their use in the diagnosis and therapy of neuronal and neoplastic diseases.

Apoplexy, also known as stroke, cerebral apoplexy and apoplectic shock, is involved in about 15% of all deaths, with men and women being affected equally. Symptoms range from disturbances of consciousness to coma, and often also encompasses spastic hemiplegia, the most disparate symptoms of central-motor and sensory loss as well as focal or generalised convulsions. Every instance of apoplexy involves a circulatory disorder in the localised cerebral region that is associated with oxygen deficiency. Two basic mechanisms act as triggers. Firstly, massive bleeding, encephalorrhagia, which is involved in 15% of cases, with this generally occurring in striolenticular arteries following vascular rupture, as a result of which limited cerebral regions are destroyed. This mechanism results in a high degree of lethality. The primary disease, which came in question, is in particular hypertonia, arteriosclerosis, intracranial aneurysm and, more rarely, consumptive coagulopathy. A cerebral infarction, encephalomalacia, is involved as the second mechanism, with this being regarded as the cause in 85% of cases. A necrosis is generally formed in this connection. Causes for this include arterial thrombosis, thromboembolism or functional ischaemia associated with open vascular lumens, e.g. following a drop in blood pressure. The cerebral infarction "ischaemic necrosis" is the cause of the apoplexy in about 70-80% of cases. Arteriosclerosis often represents the underlying causal disease. The rare, slowly developing symptoms of encephalomalacia are termed "progressive stroke". Transient symptoms of neurological loss without the formation of tissue damage ("transient ischaemic attacks") should be considered as the early signs of a cerebral infarction. A temporary stenotically induced or microembolism-induced limited circulatory disturbance is assumed to be the cause. Diagnosis encompasses not only a general and neurological examination but also cranial computer tomography, cerebrovascular Doppler ultrasound examination, spinal tap, dynamic brain scanning, EEG and nuclear spin resonance tomography.

The molecular principles of ischaemia and the associated sequelae are to date virtually unknown. However, it may be assumed that a complex series of biochemical processes is required until apoplexy occurs.

The present invention was intended to address the technical problem of identifying genes involved in the development of apoplexy following local oxygen deficiency and thus opening up new approaches to the prophylaxis and treatment of apoplexy. The present invention was further intended to address the technical problem of identifying proteins involved in the development of apoplexy.

The said technical problems are solved by a nucleic acid that codes for a serine threonine protein kinase, with the nucleic acid being selected from:

a) a nucleic acid with one of the sequences according to SEQ ID NOs. 1-4 and a nucleic acid that codes for a protein with a sequence according to one of SEQ ID NOs. 5-8;
b) a nucleic acid that hybridises with a nucleic acid according to a);
c) a nucleic acid which, taking account of the degeneration of the genetic code, would hybridise with a nucleic acid according to a);
d) derivatives of a nucleic acid according to a)-c) that are obtained by substitution, addition, inversion and/or deletion of one or more bases; and
e) a nucleic acid that is complementary to a nucleic acid according to a)-d).

For example, in derivatives of the proteins according to SEQ ID NOs. 5-8, arginine radicals are replaced by lysine radicals, valine radicals by isoleucine radicals or aspartic acid radicals by glutamic acid radicals, with the physicochemical properties of the replaced amino acid and the amino acids to be replaced being very similar (e.g. spatial filling, alkalinity, hydrophobicity). However, one or more amino acids may also be replaced within their sequence, added or removed, or several of these measures may be combined with one another. The proteins that are thus modified with respect to SEQ ID NOs. 5-8 have at least 60%, preferably at least 70% and particularly preferably at least 90% sequence identity with the sequences SEQ ID NOs. 5-8, calculated in accordance with the algorithm of Altschul et al., J. Mol. Biol., 215, 403-410, 1990. The isolated protein and its functional variants can be isolated advantageously from the brain of mammals such as *Homo sapiens, Rattus norvegicus* or *Mus musculus*. The term 'functional variants' should also be understood to mean homologues from other mammals.

The nucleic acids according to the invention according to SEQ ID NOs. 1-4 represent nucleic acids as isolated from the mouse (SEQ ID NOs. 1 and 2) or humans (SEQ ID NOs. 3 and 4) respectively, with the nucleic acids according to SEQ ID no. 2 and SEQ ID no. 4 being longer splice variants of SEQ ID no. 1 and SEQ ID no. 3 respectively. Nucleic acids that code for a protein that displays at least 60%, preferably at least 70% and particularly preferably at least 90% identity to one of the proteins as coded by SEQ ID NOs. 1-4 are also regarded as being in accordance with the invention.

"Derivatives" of the aforesaid nucleic acids according to the invention, e.g. allele variants, differ from the said nucleic acids according to SEQ ID NOs. 1-4 by substitution, addition, inversion and/or deletion of one or more bases, but with kinase activity being maintained. Derivatives, such as homologues or sequentially allied nucleic acid sequences, can be isolated from all mammalian species, including humans, by current methods via hybridisation with one of the nucleic acid sequences according to the invention or fragments thereof.

The term "functional equivalents" should also be understood to mean homologues of the nucleic acid according to SEQ ID NOs. 1-4, for example homologues from other mammals, shortened sequences, single-strand DNA or RNA or PNA of the coding and non-coding nucleic acid sequence. Functional equivalents of this kind can be isolated on the basis of the nucleic acids of SEQ ID NOs. 1-4, for example by standard hybridisation methods or PCR technology, from other vertebrates, such as mammals. Oligonucleotides from conserved regions that can be determined by the expert in the known way are advantageously used for hybridisation. However, longer fragments of the nucleic acids according to the invention or the entire sequence may also be used for hybridisation. Standard conditions for hybridisation vary according to the nucleic acid used—oligonucleotide, longer fragment or full sequence—or according to which nucleic acid type—DNA or RNA—is used for hybridisation. Thus, for example, melting temperatures for DNA:DNA hybrids are around 10° lower than those of DNA-RNA hybrids of the same length.

The term "standard conditions" should, for example depending on nucleic acid temperatures, be understood to mean between 42 and 58° C. in an aqueous buffer solution with a concentration of between 0.1-5×SSC (1×SSC=0.15 M NaCl, 15 mM sodium citrate, pH 7.2) or additionally in the presence of 50% formamide, such as for example 42° C. in 5×SSC, 50% formamide. Advantageously, hybridisation conditions for DNA:DNA hybrids are 0.1×SSC and temperatures between around 20° C.-45° C., preferably between around 30° C.-45° C. For DNA:RNA hybrids, hybridisation conditions are advantageously 0.1×SSC and temperatures between around 30° C.-55° C., preferably between around 45° C.-55° C. These specified temperatures for hybridisation are for example calculated melting temperature values for a nucleic acid with a length of approx. 100 nucleotides and a G+C content of 50% in the absence of formamide. The experimental conditions for DNA hybridisation are described in relevant genetics textbooks such as, for example, Sambrook et al., "Molecular Cloning", Cold Spring Harbor Laboratory, 1989, and can be calculated by formulae familiar to the expert, for example depending on the length of the nucleic acids, the nature of the hybrids or the G+C content. Additional information on hybridisation can be obtained by the expert from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The term "derivatives" of the sequences according to the invention according to SEQ ID NOs. 1-4 should also be understood to mean promoter variants upstream of the coding regions of the sequences according to the invention; these may be modified by one or more nucleotide replacements via insertion, addition and/or deletion without the promoter properties, particularly promoter strength and inducibility, being impaired. However, the term "derivative" also covers promoter variants which, based on the sequences according to the invention, are strengthened in their activity by nucleotide replacement(s).

"Neoplastic diseases" are those to do with abnormal growth behaviour of cells, the loss of intercellular inhibiting mechanisms, etc. These include, for example, carcinomas as abnormal proliferations of endodermal cells, lymphoneoplastic diseases, melanomas, etc.

A preferred nucleic acid codes for a protein with a sequence according to one of SEQ ID NOs. 5-8 or a protein that displays at least 60% identity to one of the said sequences.

In a further preferred embodiment, the nucleic acid is at least 60% identical to the coding sections of one of the sequences according to one of SEQ ID NOs. 1-4.

In a further preferred embodiment, the nucleic acid codes for a protein sequence according to one of SEQ ID NOs. 5-8, with a nucleic acid that codes for SEQ ID no. 7 being particularly preferred.

The nucleic acid according to the invention is preferably a DNA; however, RNA or PNA are also considered.

As fragments of a nucleic acid according to the invention, those suitable for inhibiting the expression of a serine threonine protein kinase in the antisense orientation to a promoter following incorporation in a host cell are preferred in particular. Such fragments are preferably at least 10 nucleotides, preferably at least 50 nucleotides, particularly preferably at least 200 nucleotides long.

Constructs according to the invention contain the nucleic acid sequence according to the invention or a fragment thereof in combination with other sequences, with which they are usually not associated in the genome of a host cell. Such "foreign sequences" are preferably genetic control elements, transcription and translation signals (also termed "expression-controlling elements" or sequences derived from vectors). The sequences according to the invention are functionally associated with these elements.

This association may, depending on the desired application, lead to an increase or reduction in gene expression. Host organisms can be transformed with the recombinant nucleic acid constructs thus produced. In addition to these control sequences, the natural control of these sequences of the actual structure genes may still be present and, where appropriate, have been genetically modified so that natural control has been eliminated and expression of the genes increased. The gene construct may, however, also be constructed more simply, i.e. no additional control signals are inserted upstream of the sequences and the natural promoter with its control is not removed. The natural control sequences may instead be mutated in such a way that no further control takes place and gene expression is increased. Additional advantageous control elements may also be inserted at the 3' terminal of the nucleic acid sequences according to the invention. The nucleic acid sequences according to SEQ ID NOs. 1-4 and/or sequences according to SEQ ID NOs. 5-8 that code for the corresponding proteins may be present in one or more copies in the gene construct, or be located on separate gene constructs. Advantageous control sequences are present for example in promoters such as cos, tac, trp, tet, trp-tet, lpp, lac, lpp-lac, laclq, T7, T5, T3, gal, trc, ara, SP6, I-PR or the I-PL promoter, which are preferably used in gram-negative bacteria. Other advantageous control sequences are present for example in the gram-positive promoters such as amy and SPO2, in yeast promoters such as ADC1, MFa, AC, P-60, CYC1 and GAPDH or in mammalian promoters such as CaM kinase II, CMV, Nestin, L7, BDNF, NF, MBP, NSE, beta-globin, GFAP, GAP43, tyrosine hydroxylase, kainate receptor subunit 1 and glutamate receptor subunit B. In principle, all natural promoters with their control sequences as referred to above may be used. In addition, synthetic promoters can be used advantageously. These control sequences are intended to allow for targeted expression of the nucleic acid sequences and protein expression. This may, for example, depending on the host organism, mean that the gene is expressed or overexpressed only after induction, or that it is expressed and/or overexpressed immediately. The control sequences or factors may in this connection preferably positively influence and thereby increase expression. Strengthening of the control elements may thus advantageously take place at transcription level by strong transcription signals being used as promoters and/or "enhancers". In addition, however, strengthening of translation is also possible by, for example, stability of the mRNA being improved. The term "enhancers" should be understood to mean for example DNA sequences that bring about increased expression via improved interaction between RNA polymerase and DNA. Other control sequences that can be cited include, for example, the "locus control regions", "silencers" or any sub-sequences thereof. These sequences may be advantageously used for tissue-specific expression. A preferred embodiment is the combination of the nucleic acid sequence according to the invention with a promoter, with the promoter 5' being located "upstream". Other control signals such as 3'-positioned terminators or polyadenylisation signals or enhancers may be functionally used in the nucleic acid construct. The term should also be understood to mean complete vector constructs. These vector constructs or vectors are used for expression purposes in a suitable host organism. The nucleic acids according to the invention and/or the genes for the Ser/Thr protein kinase are advantageously inserted in a host-specific vector that allows for optimal expression of the genes in the chosen host. Vectors are well known to the expert and can for example be gleaned from the book Cloning Vectors (Eds. Pouwels P. H. et al. Elsevier, Amsterdam-New York-Oxford, 1985, ISBN 0 444 904018). The term 'vectors' should, besides plasmids, also be understood to mean all other vectors known to the expert such as phages, viruses such as SV40, CMV, Baculovirus, adenovirus, Sindbis virus, transposons, IS elements, phasmids, phagemids, cosmids, linear or circular DNA. These vectors may be replicated autonomically in the host organism or chromosomally replicated. For integration in mammals, linear DNA is advantageously used. Expression of the nucleic acids sequences according to the invention or of the recombinant nucleic acid construct may be advantageously increased by increasing the number of gene copies and/or by strengthening control factors that positively influence gene expression. Thus, a strengthening of control elements may preferably take place at transcription level through the use of stronger transcription signals such as promoters and enhancers. In addition, however, strengthening of translation is possible by, for example, improving the stability of mRNA or increasing the scanning efficiency of this mRNA against ribosomes. To increase the number of gene copies, the nucleic acid sequences or homologous genes may be incorporated for example in a nucleic acid fragment or in a vector that preferably contains the control gene sequences assigned to the respective genes or promoter activity with an analogous effect. In particular, control sequences that strengthen gene expression are used. The nucleic acid sequences according to the invention may be cloned together with the sequences that code for interacting proteins in an individual vector and then expressed in the desired organism. Alternatively, each of the potentially interacting nucleic acid sequences and the sequences that code for m30 may also be placed in an individual vector and incorporated separately in the organism in question via customary methods such as transformation, transfection, transduction, electroporation or particle guns. In addition, the nucleic acid construct according to the invention or the nucleic acids according to the invention may also be expressed in the form of therapeutically or diagnostically suitable fragments. To generate the recombinant protein, use may be made of vector systems or oligonucleotides that extend the nucleic acids or the nucleic acid construct by specific nucleotide sequences and thus code for modified polypeptides that serve the purpose of simpler purification. Hexa-histidine anchors or epitopes that may be recognised as antigens of various antibodies, for example, are known as "tags" of this kind in the literature (Studier et al., Meth. Enzymol., 185, 1990: 60-89 und Ausubel et al. (eds.) 1998, Current Protocols in Molecular Biology, John Wiley & Sons, New York).

All cells that permit expression of the nucleic acids according to the invention, their allele variants, their functional equivalents or derivatives or the recombinant nucleic acid construct are in principle suitable as host cells. The term 'host cells' should be understood to mean, for example, bacteria, moulds, yeasts, plant or animal cells. Preferred host cells/organisms are bacteria such as *Escherichia coli,* Streptomyces, Bacillus or Pseudomonas, eukaryotic micro-organisms such as *Saccharomyces cerevisiae, Aspergillus*, higher eukaryotic cells from humans or animals, for example COS, Hela, HEK293, Sf9 or CHO cells. The combination from the host organism and the vectors appropriate to the organisms such as plasmids, viruses or phages such as for example plasmids with the RNA polymerase/promoter system, the phages I, Mu or other temperate phages or transposons and/or other advantageous control sequences form an expression system. The term 'expression systems' should preferably be understood to mean for example the combination of mammalian cells such as CHO cells and vectors such as pcDNA3neo vector or HEK293 cells and CMV vector that are suitable for mammalian cells. Cell-free, in vitro expression systems are, however, also considered.

Mammalian tissue, mammalian organs or transgenic mammals are also considered as hosts according to the invention for expression of the nucleic acids according to the invention. The said hosts preferably differ from the wild type in that, compared with the wild type, they contain a modified quantity of the protein according to the invention or else a new protein variant of the protein kinase according to the invention. However, host organisms in which the naturally occurring nucleic acid that codes for a protein according to the invention has been either completely or partially removed or modified in such way that it is transcription-inactive are also covered.

The said organisms preferably contain the nucleic acid according to the invention or the fragment according to the invention or the construct according to the invention integrated in a position in the genome that does not match its natural position as found in the wild type.

Mice, rats, sheep, cattle or pigs are preferably considered as transgenic mammals, although non-mammalian organisms such as plants are also considered as recipients of the sequences according to the invention. Transgenic organisms may also be what are known as knock-out animals. Transgenic animals may in this connection contain a functional or non-functional nucleic acid sequence according to the invention or a functional or non-functional nucleic acid construct. A further arrangement according to the invention for the transgenic animals described above is transgenic animals in whose germ cells or all or part of the somatic cells or in whose germ cells and all or part of the somatic cells the nucleotide sequence according to the invention has been modified by genetic engineering methods or interrupted by the introduction of DNA elements. Another possibility for use of the nucleotide sequence or parts of it is the production of transgenic or knock-out or conditional or region-specific knock-out animals or specific mutations in genetically modified animals (Ausubel et al. (eds.) 1998, Current Protocols in Molecular Biology, John Wiley & Sons, New York and Torres et al., (eds.) 1997, Laboratory protocols for conditional gene targeting, Oxford University Press, Oxford). Via transgenic overexpression or genetic mutation (zero mutation or specific deletions, insertions or modifications) by homologous recombination in embryonic stem cells, animal models can be produced that can supply additional information on the pathogenesis of apoplexy. Animal models thus produced may represent essential test systems for evaluating novel therapeutic agents.

The proteins according to the invention can be obtained by expression of one of the nucleic acids according to the invention in a suitable expression system, with expression systems comprising intact cells preferably being considered. The protein according to the invention is preferably a protein selected from a protein with one of the sequences according to SEQ ID NOs. 5-8 or a protein that is at least 60%, preferably at least 70%, particularly preferably at least 90% identical to the said sequences, with the "% identity" with the sequences according to SEQ ID NOs. 5-8 being calculated in accordance with the algorithm of Altschul et al., J. Mol. Biol, 250, 403-410, 1990. The protein according to the invention and functional variants thereof may, however, also be isolated from the brain of mammals such as *Homo sapiens, Rattus norvegicus* or *Mus musculus*. Proteins according to the invention are also those that can be derived from a protein according to one of SEQ ID NOs. 5-8 by amino acid exchange, with protein kinase activity remaining essentially unchanged. For example, amino acids in the starting protein according to SEQ ID NOs. 5-8 may be replaced by those with similar physicochemical properties (spatial filling, alkalinity, hydrophobicity, etc.). For example, arginine radicals may be replaced by lysine radicals, valine radicals by isoleucine radicals or aspartic acid radicals by glutamic acid radicals. However, one or more amino acids may also be transposed in their sequence, added or removed, or several of the said mechanisms may be combined with one another. The measures for modifying a specified amino acid sequence to a desired sequence are familiar to the expert.

The production of the antibodies according to the invention that react with a protein according to the invention is familiar to the expert. For this purpose, he may for example fall back on the production of polyclonal antisera or even hybridoma technology for the production of monoclonal antibodies.

Inhibitors according to the invention are low-molecular or even protein-like substances that can selectively inhibit or completely eliminate the protein kinase activity of the protein according to the invention. The identification and production of suitable inhibitors is quite possible for the expert via the use of conventional protein kinase assays for screening substances. Suitable screening methods and protein kinase assays are described below. Suitable substances with desired binding affinity can also be identified through the use of computer-assisted drug development (CAD) (cf. for example Böhm, Klebe, Kubinyi, 1996, Wirkstoffdesign, Spektrum-Verlag, Heidelberg). The inhibitors of protein kinase according to the invention thus identified are for example suitable for the prophylaxis and/or therapy of stroke and other neurological (particularly neurodegenerative) or neoplastic diseases. In the case of the said low-molecular substances, peptides and proteins that can enter into a specific interaction with the protein kinase inhibitor according to the invention are also considered as inhibitors. Such peptide or protein inhibitors can be identified for example with the aid of the two-hybrid system or even other assays. These assays permit the delimitation of amino acids that are responsible for a specific interaction with other interaction partners. Furthermore, the protein according to the invention and its protein kinase activity can be simply tested in a test system in which the activity of the protein is measured in the presence of the substance to be tested. Simple measurement methods (colorimetric, luminometric, fluorescence-based or radioactive techniques) that permit rapid measurement of a multitude of test substances are preferably involved (cf. Böhm, Klebe, Kubinyi, 1996, Wirkstoffdesign, Spektrum-Verlag, Heidelberg). The test systems described allow the searching of chemical libraries for substances that have inhibitory or even activating effects on proteins according to the invention. The signal transduction chain that is induced in ischaemia and proceeds via the protein according to the invention can be inhibited with these inhibitors. This allows for the inhibition or prevention of ischaemic sequelae.

The intracellular physiological interaction partners of the protein kinase according to the invention, such as phosphorylation substrate, and kinase activity-controlling intracellular interaction partners can be identified via the two-hybrid selection system mentioned above.

The protein quantity and also the activity (e.g. specific phosphorylations) of the proteins with the sequences of SEQ ID NOs. 5-8 can be determined with the aid of antibodies. A further object of the invention is therefore a method for quantifying the protein activity of a protein with one of the sequences SEQ ID NOs. 5-8. Based on the amino acid sequences according to SEQ ID NOs. 5-8, synthetic peptides can be generated that are used as antigens for the production of antibodies. It is also possible to use the polypeptide or fragments thereof for the generation of antibodies. The term "antibodies" should be understood to mean polyclonal, monoclonal, human or humanised or recombinant antibodies or fragments thereof, single chain antibodies or even synthetic antibodies. The term "antibodies according to the invention or fragments thereof" should in principle be understood to mean all immunoglobulin classes such as IgM, IgG, IgD, IgE, IgA or their subclasses such as the subclasses of IgG or their mixtures. IgG and its subclasses such as for example IgG1, IgG2, IgG2a, IgG2b, IgG3 or IgGM are preferred. The IgG subtypes IgG1/k or IgG2b/k are particularly preferred. All shortened or modified antibody fragments with one or two binding sites complementary to the antigen, such as antibody parts with a binding site formed from light and heavy chain corresponding to the antibodies such as Fv, Fab or F(ab')2 fragments or single-strand fragments, may be cited as fragments. Shortened double-strand fragments such as Fv, Fab or F(ab')2 are preferred. These fragments may for example be obtained enzymatically by cleaving the Fc part of the antibodies with enzymes such as papain or pepsin, by chemical oxidation or by genetic manipulation of the antibody genes. Genetically manipulated unshortened fragments may also be advantageously used. The antibodies or fragments may be used alone or in mixtures. The antibody genes for the genetic manipulations can be isolated in the manner familiar to the expert, for example from hybridoma cells (Harlow, E. and Lane, D. 1988, Antibodies: A Laboratory Manual, Cold Spring Harbor Press, N.Y.; Ausubel et al., (eds), 1998, Current Protocols in Molecular Biology, John Wiley & Sons, New York). To this end, antibody-producing cells are drawn in and the mRNA isolated from the cells in the known way, with adequate optical density of the cells, via cell lysis with guanidine thiocyanate, acidification with sodium acetate, extraction with phenol, chloroform/isoamyl alcohol, precipitation with isopropanol and washing with ethanol. cDNA from the mRNA is then synthesised with the aid of reverse transcriptase. The synthesised cDNA may be inserted directly or following genetic manipulation, for example by "site directed mutagenesis", introduction of insertions, inversions, deletions or base exchanges into suitable animal, fungal, bacterial or viral vectors and expressed into the corresponding host organisms. Bacterial or yeast vectors such as pBR322, pUC18/19, pACYC184, lambda or yeast mu vectors are preferred for cloning of the genes and expression in bacteria such as *E. coli* or in yeast such as *Saccharomyces cerevisiae*. Specific antibodies to the proteins according to the invention maybe suitable both as diagnostic reagents and as therapeutic agents for diseases in which the protein according to the invention is of pathophysiological importance.

The diagnostic kit according to the invention contains one of the nucleic acids according to the invention, a fragment thereof or a construct containing this, a protein according to the invention and/or an antibody specific to the protein according to the invention, and also the other reagents that usually form part of diagnostic kits. These include suitable buffer solutions and other detection reagents.

With the method according to the invention for the diagnosis of a risk of apoplexy or assessment of the course of a cerebral infarction, the patient sample is brought into contact with a nucleic acid according to the invention and the nucleic acid hybridising therewith in the patient sample is determined. An elevated level of nucleic acid that hybridises with the nucleic acid according to the invention is an indicator of an increased risk of occurrence of apoplexy. As an alternative to the detection of nucleic acid in the patient sample, the quantity of protein according to the invention can also be determined as an indicator of a risk of apoplexy. The antibodies according to the invention, for example, may be used for protein detection. An elevated protein level in the patient sample investigated is also an indicator of an increased risk of apoplexy. These assays can also be simply performed quantitatively, with the negative control representing material from a healthy patient.

Furthermore, the nucleic acids according to the invention and protein coded therefrom or oligonucleotides and peptides thereof and antibodies targeted at them may be used for the diagnosis of other diseases, particularly neurological or cardiovascular or immunological or tumour diseases. These materials may further be used for the diagnosis of genetic predispositions to specific neurological, neoplastic, cardiovascular and immunological diseases. In addition, monitoring of treatment of the said diseases can be performed with these materials.

A method for the qualitative and quantitative detection of a nucleic acid according to the invention in a biological sample comprises the following steps: a) incubation of a biological sample with a known quantity of nucleic acid according to the invention or a known quantity of oligonucleotides that are suitable as primer for amplification of the nucleic acid according to the invention, b) detection of the nucleic acid according to the invention by specific hybridisation or PCR amplification, c) comparison of the quantity of hybridising nucleic acid or of nucleic acid obtained by PCR amplification with a quantitative standard. A method for the qualitative and quantitative detection of a protein heteromer according to the invention or a protein according to the invention in a biological sample comprises the following steps: a) incubation of a biological sample with an antibody specifically targeted at the protein heteromer or at the protein according to the invention, b) detection of the antibody/antigen complex, c) comparison of the quantities of the antibody/antigen complex with a quantitative standard. A biological sample from a healthy organism is usually removed as standard. In particular, the property, as set out below, of nucleic acid according to SEQ ID NOs. 1-4 being up-regulated in accordance with specific pathophysiological stimuli, such as for example cerebral ischaemias, can be used here. This concerns for example assessment of the course of diseases (such as stroke), assessment of therapeutic success, and graduation of the severity of a disease.

The pharmaceutical composition according to the invention contains a nucleic acid according to the invention, a fragment thereof, a construct containing this, a host cell containing the said items, a protein according to the invention, an antibody targeted at it and/or an inhibitor according to the invention, where appropriate together with the customary excipients and carriers.

Therapeutic applications of the items according to the invention concern the modulation of processes connected with the phosphorylation of endogenous proteins. These include the following physiological or pathophysiological processes: influencing of immunological activation processes (e.g. activation of monocytes, T cells); influencing of cell death processes, e.g. cascades that lead to cell death, or of processes that lead to uninhibited growth. The treatable cell types include in particular neural cells, tumour cells and cells of the immune system. Lastly, cell interactions in which protein kinases are involved, e.g. cell division, cell differentiation, plasticity and regeneration, can be influenced with the materials according to the invention.

The nucleic acid according to the invention or fragments thereof and the construct containing this, the corresponding host cells and the protein according to the invention, the antibody according to the invention and/or the inhibitor according to the invention may in particular be used for the prophylaxis and/or therapy of neurological, particularly neurodegenerative diseases. These include in particular stroke, multiple sclerosis, Parkinson's disease, amyotrophic lateral sclerosis, heterodegenerative ataxias, Huntington's disease, neuropathies and epilepsies.

Tumour diseases may also be preferentially diagnosed/treated therewith. Examples of such tumour diseases include carcinomas of the colon, rhabdomyosarcoma and bronchial carcinomas.

Immunological diseases, including autoimmune diseases, atopies and/or HIV infections and coinfections, may also be diagnosed/treated by other immunotropic viruses and/or acute and/or chronic lymphatic leukaemia, and/or acute and/or chronic myeloid leukaemia and/or primary chronic polyarthritis and/or Crohn's disease and/or *Colitis ulcerosa* with the protein kinase according to the invention.

The nucleic acids according to the invention can also be used as part of gene therapy in mammals and in particular in humans. In gene therapy, the sequences according to the invention can be introduced either into the body or parts thereof or the expression of endogenous substances can be regulated, as for example by means of antisense technology. Oligonucleotides, e.g. with antisense orientation or hybrid RNA-DNA oligonucleotides that contain fragments of the sequences according to the invention may be used for this purpose. In addition, viral constructs containing a sequence according to the invention may be used. Lastly, bare DNA containing a nucleic acid according to the invention or parts thereof may be used.

The SNPs identified in the nucleic acid according to the invention are also useful for diagnosis in research into human hereditary diseases. The nucleic acids according to the invention may be used to isolate and characterise additional genes for homologous mRNAs in the murine and human genome with current methods by homology screening and correlate them with already known markers for human hereditary diseases. This permits the identification of additional genes as the cause of specific hereditary diseases.

DESCRIPTION OF FIGURES

FIG. 1 shows the principle of the Restriction-Mediated Differential Display (RMDD) method.

FIG. 2 Tissue distribution of the protein according to the invention in the rat:

The upper illustration shows a Northern Blot obtained with a mouse probe from the 3' region of SEQ ID no. 1. The lower illustration shows the ethidium bromide staining of the RNA gel shown in the upper part. A single band of the sample is detected. By far the greatest expression of the protein according to the invention is evident in the brain; clear transcripts are also still present in testis and lungs, while the other tissues display only very weak bands.

FIG. 3 shows the tissue distribution of the protein according to the invention in humans.

This shows quantitative PCR with the aid of the Light-Cycler system and use of MTC (multiple tissue cDNA) kits from the company Clontech. The strongest expression is located in the brain and lungs and the intestinal organs.

FIG. 4 shows the induction of the protein according to the invention by focal cerebral ischaemia.

This shows quantification of 9B5 mRNA with the aid of the LightCycler system following induction of focal cerebral ischaemia in mice. The nucleic acid according to the invention is up-regulated for two hours after an ischaemic episode. Six hours after ischaemia, this induction is no longer detectable.

FIG. 5 shows the induction of the protein according to the invention by focal cerebral ischaemia (in situ hybridisation of murine brain)

This shows in situ hybridisation of 9B5 following induction of focal cerebral ischaemia in mice. The nucleic acid according to the invention is up-regulated for two hours after an ischaemic episode (left=ischaemic=induced side). It is also evident that 9B5 is expressed in neurons. Specific induction is to be found in the cortex and in the hippocampal region.

FIG. 6 shows the catalytic region of SEQ ID no. 7, where the symbols have the following meaning: I=phosphate anchor, VIb=catalytic region, VII-VIII=activation loop, V-XI=catalytic domain with subdomains (after Hanks und Hunter, 1995, FASEB J., 9, 576-596); *=activation site, A=ATP binding site; C=active centre.

FIG. 7 shows the physiological tree for homologous protein kinases. H9B5 is the phylogenetically youngest protein and the most closely related to P78/c-TAK 1. The early cleaving of the C. elegans protein Par-1 is also clearly shown.

FIG. 8 shows the domain structure of 9B5.

FIG. 9 is a hydrophobicity blot according to Kyte-Doolittle.

FIG. 10 shows the genomic structure of 9B5 in humans.

This shows the 18 exons of the 9B5 gene. Exon 16 is subject to differential splicing. The variant 9B5 is formed without exon 16; the variant 9B5A contains exon 16.

Protein Sequence of 9B5

The murine protein sequences (SEQ ID NOs. 5 and 6) are incomplete at the 5' terminal. In the case of the human sequences according to SEQ ID NOs. 7 and 8, a full-length clone is involved. This also arises from alignments with homologous protein kinases.

In the case of h9B5 (SEQ ID no. 7), an open reading frame results that codes for a protein with 752 amino acids (82.5 kD molecular weight; isoelectric point at pH 9.7). The program PSORT II yields no significant signal sequences, and does not predict transmembrane regions. A Kyte-Doolittle hydrophobicity plot (FIG. 9) also shows a high proportion of hydrophilic regions and only one relatively large hydrophobic region (approx. aa 240-255) which does not, however, seem sufficiently hydrophobic for a transmembrane region (index>−3). The reported membrane-associated location of a number of related proteins (p78/c-TAK1, par1) is, however, interesting in this context.

An open reading frame of 688 amino acids with a molecular weight of 75.3 kD and an isoelectric point at pH 9.8 results for the sequence h9B5_b (SEQ ID no. 8). As a result of the insertion of exon 16, a frame shift takes place that leads to an earlier translation stop.

Classification of 9B5

A comparison with known protein kinases permits classification of the protein according to the invention to the subgroup "CaMK Group II" according to Hanks (cf. Hanks and Lindberg, Methods Enzymol, 200, 525-32, (1991); Hanks and Hunter, Faseb J, 9, 576-96, (1995))). Drewes et al. (Drewes, et al., Cell, 89, 297-308, (1997)) have already postulated for MARK1/MARK2 and p78 a new subgroup in the already defined SNF1/AMPK subgroup of the CaMKII group. Based on alignment of the most highly homologous proteins (9B5, Par1, cTAK1/p78, MARK1, EMK) and the phylogenetic tree (FIG. 7), the possibility exists that 9B5 defines a new subgroup. At the carboxy-terminus, 9B5 deviates sharply from the other protein kinases. The kinases in this group are characterised by a highly conserved carboxy-terminus domain that terminates with the sequence "ELKL" SEQ ID NO. 9. EMK has therefore also been designated as "ELKL SEQ ID NO. 9 motif kinase". It should be assumed that protein kinases still exist that are similar to 9B5 in the carboxy-terminus and that can be identified via homology screens. A search with the program "tblastn" against the EMBL nucleotide database has to date yielded no evidence of already known homologues in the carboxy-terminus region.

Proteins with the target sequence KXGS SEQ ID NO. 10 and/or KVGS SEQ ID NO. 11 may form the physiological substrate of the protein according to the invention. Accordingly, the Tau protein or the proteins MAP1 and 2 may represent a physiological substrate of the protein kinase according to the invention.

Subdomains of the Catalytic Domain: 9B5 is a Serine Threonine Protein Kinase

The important catalytic subdomains can be clearly defined via comparisons with other protein kinases (see FIG. 6). The activation sites can likewise be shown (a threonine and a serine that may be phosphorylated; pos. 211 and 215 in h9B5, FIG. 6). A mutation of these amino acids, for example to alanine, leads to constitutive inactivation. Mutation of the lysine radical (ATP binding) in subdomain II (see FIG. 6) likewise leads to inactivation. This finding can be utilised for further experiments, e.g. using dominant negative effects. A mutation of pos. 211 (Ser) and 215 (Thr) to glutamate or aspartate should lead to constitutive activation as the negatively charged groups may imitate phosphorylation (Huang and Erikson, Proc Natl Acad Sci USA, 91, 8960-3, (1994)). These mutants may be exploited for overexpression of the specific kinase activity in cells or transgenic animals.

Subdomain I is known to act as a kind of clasp that anchors the non-transferrable phosphate groups of ATP. In this connection, the peptide sequence GKGNFAKV SEQ ID NO. 12 in 9B5 fits in well with consensus motif GXGXXGXV SEQ ID NO. 13 (Hanks and Hunter, *Faseb J,* 9, 576-96, (1995)). In subdomain II, chiefly lysine (labelled "A" in FIG. 6) is important; this anchors and orientates the alpha and beta phosphates of ATP and is essential for enzyme function. Subdomain VIb is characterised by the consensus sequence HRDLKXXN SEQ ID NO. 14 . This is also very well preserved in 9B5: HRDLKAEN SEQ ID NO. 15.

Aspartate (D) is in this connection probably the proton acceptor for the attacking hydroxyl group during the phosphotransfer reaction (Hanks and Hunter, *Faseb J,* 9, 576-96, (1995)). Subdomain VII forms with Mg2+ ions a chelate complex that encloses the gamma-phosphate and thus orientates this group for the transfer. The sequence DFG is practically invariable. The preserved sequence APE in subdomain VIII is similarly maintained. This domain is responsible for peptide recognition. Inhibitor peptides can also bind here. Many protein kinases are activated by phosphorylation within this subdomain. This domain is fully preserved in EMK, p78 and MARK1. In the case of MARK1, it has already been shown by direct sequencing that threonine (T) and serine (S) can be phosphorylated, and MARK1 is thereby activated. Owing to this preservation, it may be assumed with the utmost probability that 9B5 also phosphorylates at these sites and thus can be controlled. Autophosphorylation possibly takes place; activation by another kinase is also conceivable. The tyrosine (Y) in this domain is possibly also a phosphorylation site (as for example in the case of Erk1/2). Subdomain IX is also involved in peptide binding (hydrophobic interaction).

On account of this structural development, it can be assumed with certainty that 9B5 is an active protein kinase (serine threonine kinase).

Tissue Expression of 9B5

The tissue expression of 9B5 has been investigated in mice and humans. In mice, a "multiple tissue northern" was performed with various tissues (FIG. 2). A fragment from the 3' region of the mouse cDNA was used as sample. Here, expression takes place in the brain, testicles and lungs.

In humans, a "multiple tissue northern" (Clontech) was initially performed with 2 different probes (from the 3' and 5' regions). However, no clear signal could be obtained, which was attributed to the low incidence of 9B5 in humans. A quantitative PCR was therefore performed with the aid of the LightCycler (Roche Diagnostics, Mannheim). cDNA samples of 8 human tissues already quantitatively standardised on 4 different housekeeping genes were used (manufactured by Clontech). Plasmid h9B5-663, which contained an amplified fragment of human 9B5-cDNA, was used as control. A touchdown protocol was chosen as PCR program. Amplification of a product with a melting point of 90° C. took place in all tissue samples; this coincided with the control PCR. A subsequent gel analysis of the fragments yielded a product of approx. 660 bp, i.e. the expected size. 9B5 in humans is actually not very strongly expressed; amplification becomes visible in the LightCycler only at around cycle 32. The following primers were used:

```
seq_h9b5_s1  GTTGCCATCAAGATTATC      SEQ ID NO. 16 (in
                                                   exon
                                                   3)

seq_h9b5_a4  CATGATTTGCTCGAGAGTAC    SEQ ID NO. 17 (in
                                                   exon
                                                   9)
```

Quantitative analysis (FIG. 3) shows a relatively ubiquitous tissue distribution with higher concentrations in the brain and lungs, liver, kidneys and pancreas.

Regulation by Focal Cerebral Ischaemia, a Stroke Model

The serine threonine kinase 9B5 according to the invention was identified by a method for the cloning of differentially regulated genes (RMDD) in the ischaemic hemisphere of mice following focal cerebral ischaemia. The animal model for focal cerebral ischaemia represents a valid model for human ischaemic stroke. To bring about the focal cerebral ischaemia, use was made of the so-called thread model, in which a coated nylon thread is passed through the A. carotis interna up to the end of the A. cerebri media and induces an ischaemic stroke (Clark et al., *Neurol. Res.,* 19, 641-648, (1997)). In cerebral ischaemia, regulation of gene expression plays a crucial role in the course and extent of neuronal damage (Koistinaho and Hokfelt, *Neuroreport,* 8, i-viii, (1997, Schneider et al., *Nat Med,* 5, 554-9, (1999)). In particular, "immediate early" genes play a role here (Atkins et al., *Stroke,* 27, 1682-1687, (1996)), such as cox-2, (Nogawa et al., *J. Neurosci.,* 17, 2746-2755, (1997)).

9B5 expression was, following focal cerebral ischaemia, investigated over three timescales: firstly, in a transient ischaemia following two reperfusion periods (ischaemia for 90 mins, reperfusion for 2 h and 6 h), and secondly in a permanent ischaemia of 24 h (FIG. 4). RNA was extracted from the two hemispherical halves of 3-4 brains without brain stem and cerebellum (Fasttrack kit, Invitrogen). With the aid of the LightCycler™ system (Roche Diagnostics, Mannheim), a quantitative PCR was performed. The cDNA content of the samples was standardised to the expression of cyclophilin and S20 (Schneider et al., *Proc Natl Acad Sci USA,* 92, 4447-51, (1995)). The primers used for the amplification of cyclophilin were:

```
cyc5      ACCCCACCGTGTTCTTCGAC    SEQ ID NO. 18 acyc300   CATTTGCCATGGACAAGATG    SEQ ID NO. 19
``` and for the amplification of murine 9B5:
9_B5_(1)_1s TATGATCGAACCTCCTTCATGCC SEQ ID NO. 20
9_B5_(1)_1a ATGTCCAGAACTGGGCCTAGCG SEQ ID NO. 21 (These primers amplify an amplimer of 556 bp, which is located at the 3' terminal of the murine cDNA).

In actual fact, clear up-regulation of 9B5-RNA by a factor of 7-8 on the ischaemic (left) half of the brain appears 2 h after the ischaemic event (middle cerebral artery occlusion for 90 mins and reperfusion for 2 h; (FIG. 4); the error bars show standard deviations—these arise from measurements with thrice serially diluted cDNA samples and thus reflect the reliability of the measurement results). After 24 h (in a permanent model), on the other hand, no difference was any longer detectable.

In-situ hybridisation was also performed with a 1.6 kb long probe from the 3' region of murine 9B5-cDNA (sense and antisense in each case). The procedure adopted for this was essentially as per the protocol of the company Roche Diagnostics (digoxigenin system) following modifications by Rossner et al. (Mol Cell Neurosci, 9, 460-475, (1997)). Clear induction is apparent on the ischaemic side (left), particularly in neurons of the hippocampal region and cortex, less so in the thalamus (FIG. 5). It also becomes clear that 9B5 is predominantly expressed in neurons, and is subject to control there.

This shows that 9B5 plays an important role in the pathogenesis of stroke, with the up-regulation of 9B5 playing a similar role to that, for example, of the known serine threonine kinases (e.g. JNK, p38).

A multitude of serine threonine kinases are involved in cell death processes (e.g. ASK1 (Tobiume, et al., *Biochem Biophys Res Commun*, 239, 905-10, (1997, Berestetskaya, et al., *J Biol Chem*, 273, 27816-23, (1998, Chen, et al., *Oncogene*, 18, 173-80, (1999)), DAP (Inbal, et al., *Nature*, 390, 180-4, (1997, Levy-Strumpf and Kimchi, *Oncogene*, 17, 3331-40, (1998)), DRAKs (Sanjo, et al., *J Biol Chem*, 273, 29066-71, (1998)), ZIP (Kawai, et al., *Mol Cell Biol*, 18, 1642-51, (1998))), DRP-1 (Inbal, et al., *Mol Cell Biol*, 20, 1044-54, (2000)).

This up-regulation is evidence of a new transcriptional control mechanism for protein kinases, to date the only known example of this in the mammalian system. Interestingly, the up-regulation of several MAP kinases was only very recently found in a systematic study of the yeast transcriptome (Roberts, et al., *Science*, 287, 873-80, (2000)). This might represent a new general mechanism for the regulation of protein kinases.

Pharmacological Significance of 9B5 in Neurodegenerative, Neoplastic and Other Diseases Approaches to inhibiting/influencing signal transduction pathways "downstream" of a membrane-based receptor have recently been gaining in importance in pharmacological research. These approaches will in future probably play an important part in the treatment of human diseases, particularly in the case of diseases that have hitherto been poorly treatable or untreatable (Kletsas and Papavassiliou, *Exp. Opin. Invest. Drugs*, 8, 737-746, (1999)). Advantages of these approaches are that they can first influence events that can be brought about by several stimuli, and have a common terminal section; secondly, cellular events temporally follow the triggering stimulus, and are thus open to intervention for longer.

Examples of successful interventions in such signal cascades include inhibitors for caspases that can block apoptosis processes for even longer after a triggering stimulus. The transcription factor NF-kappaB and these activating processes have also attracted particular attention. For example, cloning of the I-kappaB kinases was pursued with the aim of finding specific inhibitors for NF-kappaB-mediated gene transcription. Differential transcription profiling has recently been gaining in importance in pharmaceutical research to identify possible new points of departure for drugs. Transcriptional control, i.e. control of the quantity of mRNA in a gene in the cell, is an essential stage in the cell's response to stimuli, in addition to protein phosphorylations, protein degradation, etc. 9B5 is evidently subject to very rapid control by transcriptional activation, as shown above. Rapidly controlled genes of this kind are often involved in critical key positions for cellular processes.

A pharmacological influence on 9B5 is possible in the following way: 1. an effect on the quantity of transcript in the cell, for example suppression of rapid up-regulation following pathological processes (e.g. via antisense technology); 2. inhibition of the enzymatic activity of 9B5, particularly kinase activity (e.g. via a kinase inhibitor; 3. inhibition of an interaction with one or more other molecules, e.g. downstream protein kinases or adaptors.

Specific inhibitors for a number of MAP protein kinases have been developed recently. One example is PD98059, an inhibitor of MEK1. This prevents the phosphorylation of Tau by stimulation with beta-amyloid. This has possible significance for the treatment of Alzheimer's disease.

The antitumour substance UCN-01 is an inhibitor of cdc25c phosphorylation (Graves, et al., *J Biol Chem*, 275, 5600-5, (2000)).

Inhibitors of the protein kinase according to the invention can be simply identified with conventional protein kinase assays and represent an effective aid in controlling the sequelae of cerebral ischaemia.

The experimental data on 9B5 prove its central involvement in processes associated with neuronal cell death, excitation, plasticity and neurogenesis. The protein according to the invention represents an important target molecule for inhibiting or reducing the sequelae of focal ischaemia. Besides this central role in the development of apoplexy as a consequence of focal ischaemia, the protein according to the invention might also be an important target molecule in the treatment of neoplastic diseases, such as cancer. Here, too, the protein according to the invention or its gene might represent the target molecule for anticancer agents. The gene might likewise play an important role in the diagnosis and therapy of cardiovascular diseases as a number of shared mechanisms exist for ischaemically induced diseases.

In a particularly preferred embodiment according to the invention, the level or activity of the protein kinase according to the invention is lowered for the prophylaxis and therapy of stroke. This may for example take place at the level of expression, by expression/translation of the corresponding nucleic acids being inhibited or reduced, or at the level of protein activity, by protein kinase activity being reduced or inhibited by suitable inhibitors.

The nucleic acid according to the invention and the protein coded therefrom open up new therapeutic approaches. Thus, for example, the level of endogenous nucleic acid can be influenced by either directly influencing its transcription or even influencing its translation to protein according to the invention. For example, gene therapy approaches are considered for this in which, via co-suppression or antisense technology, the translation of endogenous transcripts is lowered. New approaches also present themselves at the level of protein activity by the protein according to the invention for example representing the target molecule of pharmaceutical active substances. Thus, the activity of protein kinase according to the invention can be modified by pharmaceutical active substances in order to intervene in a controlling way in the mechanism of apoplexy. The protein kinase inhibitors mentioned above represent a class of such pharmaceutical active substances. In principle, provision of the nucleic acid according to the invention or the protein according to the invention thus also opens up entirely new approaches to the prophylaxis or therapy of stroke.

The following examples elucidate the invention:

EXAMPLES

Example 1

Molecular Cloning of 9B5

Induction of the Thread Model in Mice

To induce focal cerebral ischaemia in c57/bl6 mice, 3-month-old mice were used. Following induction of an inhalation anaesthesia (70% $N_2O$, 30% $O_2$, 0.8-1% halothane), a 5-0 prolene thread (manufactured by the company Ethicon) coated with 0.1% poly-L-lysine was passed via the A. carotis externa into the A. carotis interna up to the end of the A. cerebri media. The correct position of the thread is indicated by a drop in the laser Doppler signal (Perimed company) to 10-20% of the starting signal. Following the performance of this operation and, where appropriate, determination of additional physiological parameters (blood pressure, pulse, blood gases, blood glucose), the mice wake from the anaesthesia. After specific occlusion periods, the mice are again subjected to anaesthesia, and the thread is withdrawn. Reperfusion of the tissue thereby takes place. Following specific reperfusion periods, the mice are sacrificed by breaking their necks, and the brains immediately prepared and frozen in dry ice.

In the present case, no reperfusions were performed, only an occlusion for 90 mins or 24 h.

Preparation of mRNA from the Brains

The mRNA preparation kit manufactured by Invitrogen (Fasttrack) was used for this purpose.

Performance of the RMDD Protocol (see also FIG. 1)

The procedure adopted was essentially as per Pat. No. EP 0 743 367A2; U.S. Pat. No 5,876,932, with the modification that 2 μg polyA-RNA was used for the first-strand synthesis. Following performance of first-strand, second-strand synthesis, MboI restriction, ligation with adaptors is performed. Two successive PCR reactions with subsets of primer combinations follow. The PCR reactions are then loaded onto a denaturing polyacrylamide gel and blotted on a nylon membrane (manufactured by GATC). The biotin-labelled bands are visualised with the aid of an ordinary streptavidin peroxidase reaction. PCR samples of the ischaemic and contralateral hemisphere were applied together to the gel (24 h MCAO on the right and left and 90 mins MCAO on the right and left). Bands of differing intensity in the right or left hemisphere are cut out, and reamplification of the corresponding PCR product performed. Amplified products obtained are cloned into TOPO TA vector pcDNA 2.1 (manufactured by Invitrogen) and sequenced with T7 and M13rev primers (ABI 3700 capillary electrophoresis sequencer).

Cloning of 9B5

During the performance of this method, a sequence was noticed that seemed to be up-regulated after 90 mins on the ischaemic side. This was called 9B5. A LightCycler analysis confirmed rapid regulation after MCAO (90 mins MCAO and 2 h reperfusion) (FIG. 4).

The isolated 3'-positioned PCR fragment was used to hybridise a murine brain bank, in which there were several clones that contained sequence parts of SEQ ID no. 1 and SEQ ID no. 2. A mouse sample from the 5' region was used to screen a humane foetal brain bank in lambdaZapII (Stratagene). In this connection, 2 different sequences also resulted from several clones, which presumably represent splice variants of the same gene (SEQ ID NOs. 3 and 4), resulted from several clones.

The detailed production of the human cDNA library used is set out below:

Production of the Human cDNA Library

Using the cDNA synthesis kit manufactured by the company Stratagene, corresponding cDNA libraries were, on the basis of 2 μg human foetal brain mRNA (manufactured by Clontech) and 5 μg mRNA, produced from adult murine brain, with the procedure adopted essentially being in accordance with the manufacturer's details. To synthesise the first-strand cDNA, an oligodT primer was used in accordance with the manufacturer's details. The cloning-compatible (EcoRI/XhoI) double-stranded cDNA fragments were selected by size (in accordance with manufacturer's details/Stratagene) and ligated into the plasmid vector pBluescript SKII (Stratagene). The ligation was transformed by electroporation in *E. coli* (DH10B, Gibco) and amplified on LB ampicillin agar plates. The plasmid DNA was isolated via alkaline lysis and ion exchanger chromatography (QIAfilter kit, manufactured by Qiagen).

The complexity of individual clones was 4 million for the foetal human brain cDNA bank. From each cDNA bank, 24 individual clones were randomly analysed by insert sizes, which showed a size distribution of 800 bp to 4.5 kB; the mean length of the cDNA inserts was for the human bank approx. 1.2 kB.

Example 2

Performance of a Reporter Gene Assay

The sequence of 9B5 obtained can be used to obtain information on the arrangement of the protein in signal transduction cascades. To this end, the open reading frame of the gene is cloned into a current expression vector (e.g. pCMV-tag, manufactured by Stratagene). This construct can be transfected with other constructs together in eukaryotic cells (e.g. by the calcium phosphate method, see Ausubel et al., Current Protocols in Molecular Biology, New York, 1997). These may be reporter constructs, e.g. a luciferase gene under the control of a minimal promoter with several binding sites for, for example, the transcription factor NF-kappaB or AP-1. Extracts from the cells may then be subjected to measurement in the luminometer (e.g. manufactured by the company Bertold). An increase in the luciferase value indicates influencing of the signal transduction pathway that results in the activation of a specific transcription factor. Combinations with expression constructs for other genes (e.g. MAP kinases) may provide information on the precise position of 9B5 in signal cascades. These reporter assays can also be performed with other systems, e.g. lacZ or chloramphenicol transferase (CAT assays), without the principle of the assays being influenced.

In the same way, ready-made kits (e.g. Mercury in vivo kinase assay kits, manufactured by Clontech) may also be used, with the Tet repressor being expressed in fusion with the transactivator domain of a phosphorylation target (transcription factors, e.g. Jun). Activation of a luciferase construct under the control of a Tet repressor element only takes place if specific phosphorylation of the transactivator domain by a kinase (e.g. 9B5) occurs. In this way, arrangement in a cellular signal transduction pathway is possible.

Example 3

Kinase Assays

Protein kinases are biochemically very well characterised. The kinase activity of 9B5 can be demonstrated by cloning the open reading frame of 9B5 into an expression vector with an epitope tag (e.g. pcDNA-myc-his) and transfecting it in eukaryotic cells (e.g. Cos cells). After 48 h, extracts can be obtained from these cells and immunoprecipitation performed with a myc-specific antibody and proteinA beads. In a kinase buffer in the presence of $\gamma$-$^{32}$P-ATP, a kinase reaction is performed. The proteins are then denatured and separated on an SDS-PAGE gel. Autoradiography is then performed. Labelled bands indicate the kinase activity of 9B5. Autophosphorylation of the kinase itself often takes place as well. Indications of possible phosphorylation targets are also provided by cotransfections with potential targets, e.g. various MAP kinases that are also provided with a tag and can be immunoprecipitated.

Kinase assays may also be performed with 9B5 that has been transcribed/translated in vitro (e.g. T7 reticulocyte system manufactured by the company Promega). Protein that has been expressed in *E. coli*, e.g. as GST fusion protein or as HIS-tagged construct, can also be used. These tags may in this connection be used for purifying the protein. The purified proteins can then be incubated in kinase buffer with potential substrates. MBP (myelin basic protein) that is frequently non-specifically phosphorylated by Ser/Thr kinases is often used here.

The kinase domain of protein kinases is very well defined. The mutation of individual amino acids in the phosphate transfer domain is often sufficient for loss of function of the protein (e.g. K709M in the case of ASK1 (Chang et al., *Science*, 281, 1860-3, (1998)); K90A in DRAK 1, K62A in DRAK2 (Sanjo et al., *J Biol Chem*, 273, 29066-71, (1998)); KK429-430AA in NIK (Sanjo et al., *J Biol Chem*, 273, 29066-71, (1998)); K63W in TAK1 (Ninomiya-Tsuji et al., *Nature*, 398, 252-6, (1999))). These inactive kinases are often of great importance as dominant-negative inhibitors for evaluation of the cell pathways, e.g. in cotransfection experiments and kinase assays (Ninomiya-Tsuji et al., *Nature*, 398, 252-6, (1999)). Mutation of this kind can also be performed with 9B5.

The specific phosphorylation of target protein can also be demonstrated with phosphorylation-specific antibodies, e.g. Phospho-SerThr/Tyr monoclonal antibody, mouse IgG2b, produced by the company Clontech.

Further examples of kinase assays that are commonly used in the technical arena can, for instance, be gleaned from the book Protein Phosphorylation, A practical approach, ed. D. G. Hardie, 2nd ed., Oxford, 1999, particularly chapters 9 and 10.

Example 4

Identification of the Phosphorylation Target of 9B5

The identification of phosphorylation targets of 9B5 may, for example, take place via interaction screening. Somewhat classic peptide expression banks in the lambda bacteriophages (the most used system is the vector lambda-gt11, see Ausubel et al., Current protocols in molecular biology, New York, 1997) may be used in this connection. One approach is the cloning of 9B5 into a bacterial expression vector with the incorporation of a purification tag (e.g. poly-histidine or GST) and a consensus phosphorylation site for protein kinase A (sequence RRASV). 9B5 may thus be expressed and purified in bacteria in accordance with standard methods. 9B5 can in this way be labelled as a scavenger with $^{33}$P or $^{32}$P by means of incubation with protein kinaseA. The expression bank can then be incubated with the labelled 9B5. Following exposure on autoradiograms, positive clones can be identified and be isolated and sequenced by standard methods. This technique can also be adapted in the following way: the autophosphorylation property of 9B5 can be utilised to label 9B5 with $^{33}$P-γATP via simple incubation. The method can also be modified in such a way that the expression bank is incubated with purified 9B5 and $^{33}$P-γATP under phosphorylation conditions (phosphorylation buffer, etc.), and expressed peptides are actively labelled by 9B5. However, this method is more unstable than that described above. Sequenced peptides can be used to formulate a consensus recognition and phosphorylation sequence. This permits the identification of potential substrates via bioinformatic methods. Candidates can be verified by expression and incubation with 9B5. Examples of the successful performance of these forms of expression screening are contained in (Mochly-Rosen and Gordon, *Faseb J*, 12, 35-42, (1998, Blanar and Rutter, *Science*, 256, 1014-8, (1992, Chapline et al., *J Biol Chem*, 268, 6858-61, (1993, Chapline et al., *J Biol Chem*, 271, 6417-22, (1996, Kaelin et al., *Cell*, 70, 351-64, (1992, Songyang et al., *Curr Biol*, 4, 973-82, (1994)).

The phosphorylation target of 9B5 can also be identified in a yeast-two-hybrid screen (Fields and Song, *Nature*, 340, 245-6, (1989)). For example, the interaction of Ras and c-Raf (a Ser/Thr kinase) was discovered in a y2h system (Fields and Song, *Nature*, 340, 245-6, (1989)). Interaction of the Ser/Thr kinase SNF1 with SNF4 is also virtually a prototype for the y2h system (Fields and Song, *Nature*, 340, 245-6, (1989)). In principle in an equivalent way to the yeast screens, mammalian systems can also be used (Fields and Song, *Nature*, 340, 245-6, (1989)). In the case of a y2h screen, the open reading frame of 9B5 is cloned into a so-called "bait vector" with the GAL4 binding domain (e.g. pGBT10, manufactured by Clontech). A so-called "prey-library" in a yeast strain can thus be searched for interacting proteins in accordance with several current protocols. It can in this connection often be useful to use kinase-negative mutants as these often interact in a more stable manner with the phosphorylation target. Serine threonine kinases in a synthesis pathway may be brought into spatial proximity by adapter molecules in order to be able to perform specific phosphorylations better (Chang et al., *Science*, 281, 1860-3, (1998)), (Yasuda et al., *Mol Cell Biol*, 19, 7245-54, (1999, Whitmarsh and Davis, *Trends Biochem Sci*, 23, 481-5, (1998, Whitmarsh et al., *Science*, 281, 1671-4, (1998)). It is therefore also possible to encounter the phosphorylation targets via two steps in the yeast-two-hybrid system by first cloning an adaptor protein and finding the specific target molecule with this as "bait". All in all, mapping experiments for interaction domains can also be performed with the y2h system.

It is also possible to use co-immunoprecipitations from cells transfected with 9B5 expression vectors to purify proteins binding to them, and to identify the genes via protein sequencing methods (e.g. MALDI).

It is also possible, following immunoprecipitation with a subsequent kinase assay from a cell extract, to purify the phosphorylated bands and to sequence these.

Further examples of the identification of protein kinase substrates that are commonly used in the technical arena can be gleaned from, for instance, the book Protein Phosphorylation, A practical approach, ed. D. G. Hardie, 2nd ed., Oxford, 1999.

Example 5

Apoptosis Assays

Very many previously identified serine threonine kinases are involved in apoptotic processes, e.g. ASK1 (Zhang et al., *Proc Natl Acad Sci USA*, 96, 8511-5, (1999)), (Ichijo et al., *Science*, 275, 90-4, (1997)), DRAKs (Zhang et al., *Proc Natl Acad Sci USA*, 96, 8511-5, (1999)), (Ichijo et al., *Science*, 275, 90-4, (1997)). The involvement of 9B5 in apoptotic cascades can be further investigated by transfecting expression constructs with 9B5 in eukaryotic cells, and then investigating the induction of apoptosis. This may, for example, take place via staining with annexin (manufactured by Roche Diagnostics), by antibodies that recognise the active form of caspase-3 (manufactured by New England Biolabs), or by ELISAs that recognise DNA-histone fragments (cell-death elisa, Roche Diagnostics). This induction of apoptosis may be cell type-specific, and so several cell lines and primary cells must be investigated. The induction of apoptosis may also be stimulus-specific, and so several stress situations may be helpful in answering this question, e.g. heat shock, hypoxia conditions, cytokine treatments (e.g. Il-1, Il-6, TNF-alpha), $H_2O_2$ treatment. On cell types, several customary lines, e.g. Cos cells, HEK cells, PC12 cells, THP-1 cells and primary cells such as, for example, neurons and astrocytes are considered, as are other immortalised and primary cell lines, as required.

Example 6

High-Throughput Screening Assays for the Identification of Inhibitors of 9B5

9B5 can be used to find inhibitors of the interaction with its interaction partners (e.g. adaptor molecules). This can be performed, for example, with the FRET (frequency resonance energy transfer) system by 9B5 being expressed in fusion and purified with GFP (green fluorescent protein) and its interaction partner with BFP (blue fluorescent protein). In a cell-free system, the reduction in emission of BFP can then be used as an indicator of the presence of an inhibitor when searching complex chemical banks.

The main aim behind therapeutic exploitation of the protein kinase detected is, however, firstly to eliminate the protein kinase function, as this can be performed most easily. Protein kinases present themselves in principle for the performance of high-throughput assays for the identification of inhibitors (small-molecule inhibitors) of the kinase property of the protein as the enzyme property itself can be readily used as indicator (see also example 3, kinase assays).

Simple implementation of an HTS system for 9B5 can be performed by the filter assay method of Reuter et al. (Reuter et al., *Methods in Enzymology*, 255: 245 (1995)), with MBP being used as non-specific substrate. This is applied to 96-hole plates that are suitable for ELISA (e.g. FlashPlates, NEN Life Science Products, or NUNC). Reaction buffer (3× kinase reaction buffer contains: 60 mM HEPES (pH 7.5), 30 mM MgAc, 0.15 mM gammaATP, 3 mM DTT, 0.03 mM Na-orthovanadate) is added. 0.25 µCi 33P-gamma-ATP and the kinase described are added in a concentration of no more than 1 µg/ml (a titration should first be performed). In the presence of the potential inhibitor (e.g. small molecules from a chemical bank) (e.g. 10 µM), the reaction is incubated at 30° for 1 h. The total reaction volume is 100 µl. The reaction is stopped by the addition of EDTA (pH 7) up to a final concentration of 80 mM. The samples are then centrifuged, and 50 µl of the supernatant is applied to p81 cation exchanger paper (manufactured by Whatman). The filters are then washed 3 times in 200 ml 180 mM phosphoric acid (every 5 mins), and once in 200 ml 96% ethanol. Following drying in air, the radioactivity of the filters is determined by scintillation counting. Substances that reduce kinase activity by >=50% (at 10 µM) stand out as a result of a >50% reduction in incorporation. The specificity and sensitivity of the possible inhibitors are determined by titration to determine IC50, and by substitution of other kinases in the assay. Relative comparisons of the inhibition effect on other kinases thus allow for a measure of specificity.

For the performance of screens on kinase inhibitors, more modern systems with the scintillation proximity assay (SPA) also present themselves (manufactured by Amersham Life Science, MAP kinase SPA; (Zhang et al., *Proc Natl Acad Sci USA*, 96, 8511-5, (1999)), (Ichijo et al., *Science*, 275, 90-4, (1997))). McDonald describes an assay set-up for the Raf/MEK/ERK cascade that can identify inhibitors of the entire cascade. A biotinylated peptide which, following phosphorylation with $^{33}P$, can bind to avidin-coated SPA beads is used here. The MAP cascade is here reconstituted in vitro, expressed with the individual constituents as GST fusion protein in *E. coli* or, in the case of cRAF1, produced with the Baculovirus system. The first element of the cascade (MAP-KKK) must in this connection always be uniformly activated to be able to screen inhibitors reliably. This was achieved in this case by coexpression of src in the Baculovirus system. A ras-analogous activation of cRaf is thereby achieved. Another way of activating a MAP kinase by phosphorylation is also conceivable in principle. Another possibility of constitutive activation of a MAP kinase consists in mutation of the amino acids to be phosphorylated. This was, for example, possible in the case of MEK1 via the replacement of the serines Ser218 and Ser222 by glutamate (Zhang et al., *Proc Natl Acad Sci USA*, 96, 8511-5, (1999)), (Ichijo et al., *Science*, 275, 90-4, (1997)). In the case of 9B5, an interaction screen (e.g. y2h system) can firstly be performed to identify a phosphorylation target or MBP (myelin basic protein) directly used as substrate. A peptide from the target sequence can then be synthesised with a biotin anchor. This can bind to avidin-coupled SPA beads manufactured by Amersham. Purified (e.g. bacterially produced) 9B5 protein and gamma-32P-ATP are still added during the reaction. This can take place on a microtitre scale. Under normal conditions, the target peptide is phosphorylated and will trigger a scintillation response. From a library of chemical substances, those with the reaction will now be pre-incubated prior to addition of the target peptide. Following addition of the target peptide, the scintillation response can then be measured. A drop in response signifies the presence of a potential inhibitor. The library searched should be as complex as possible, and contain many different substance classes. Examples of a substance class-specific inhibitor for a protein kinase (p38) can be found for example in U.S. Pat. No. 5,945,418. Other substance classes that can inhibit protein kinases are for example bis monocyclic, bicyclic or heterocyclic aryl compounds (WO 92/20642), vinylene-azaindol derivatives (WO 94/14808), 1-cyclopropyl-4-pyridyl-quinolone (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), Selenoindoles and selenides (WO 94/03427), tricyclic polyhydroxylic compounds (WO 92/21660), and benzylphosphonic acids (WO 91/15495).

The specific nature of the assay is solely determined by the identity of the Ser/Thr kinase described. Various substrates can be used. These may be used in various forms of the aforementioned assay principle. The essential point in this is, however, always the use of the kinase activity of 9B5 for screening purposes. For example, the substrate may occur in free solution as well as being coupled to a phase, as mentioned above. The substrate may, however, also be borne on a cell surface or even be presented intracellularly. This does not affect the underlying assay principle.

Example 7

Production of Transgenic and Knock-Out Mice

Knowledge of the sequence of 9B5 can be used to produce genetically modified mice (or other animals). To this end, for example a constitutively inactive mutant of 9B5 is expressed in transgenic mice, e.g. with an NSE promoter in neurons, with an MBP promoter in oligodendrocytes, etc. This should have a dominant-negative effect, and thus imitate inhibition of 9B5. This may yield valuable indications of possible pharmacological effects of inhibitors in vivo. A constitutively active kinase can also be expressed.

The production of knock-out animals may also yield indications of the effects of inhibitors. The production of these genetically modified mice or other animals takes place in accordance with standard methods familiar to the expert.

The genetically modified animals can then be investigated in various disease models (e.g. experimentally induced stroke, MCAO), or tumour models.

Example 8

Proliferation Assays

Many of the previously known serine threonine kinases are involved in neoplastic processes. The involvement of 9B5 in the growth of cells, the cell cycle and tumorigenic transformation can be further investigated by transfecting expression constructs with 9B5 in eukaryotic cells and then investigating the induction of tumorigenicity, e.g. in a Soft-Agar test (Zhang et al., *Proc Natl Acad Sci USA*, 96, 8511-5, (1999)), (Ichijo et al., *Science,* 275, 90-4, (1997)). On cell types, several customary lines, e.g. Cos cells, HEK cells, PC12 cells, THP-1 cells and primary cells, such as for example neurons and astrocytes, are considered, as are other immortalised and primary cell lines, as required.

The invention claimed is:

1. An isolated nucleic acid that codes for a neuronal serine threonine protein kinase, selected from the group consisting of
   a) a nucleic acid comprising SEQ IID NO: 4; and
   b) a nucleic acid that codes for a protein comprising SEQ ID NO: 8; and
   c) a nucleic acid that codes for a protein having serine threonine kinase activity, wherein said protein exhibits at least 90% identity to a protein comprising SEQ ID NO: 8.

2. A nucleic acid according to claim 1 that codes for a protein sequence comprising SEQ ID NO: 8.

3. A nucleic acid according to claim 1, wherein the nucleic acid is a DNA.

4. A nucleic acid construct comprising an isolated nucleic acid selected from the group consisting of
   a) a nucleic acid comprising SEQ ID NO: 4; and
   b) a nucleic acid that codes for a protein comprising SEQ ID NO: 8; and
   c) a nucleic acid that codes for a protein having serine threonine kinase activity, wherein said protein exhibits at least 90% identity to a protein comprising SEQ ID NO: 8.

5. A nucleic acid construct according to claim 4, wherein the construct is present in a plasmid.

* * * * *

SEQUENCE LISTING

```
<160> NUMBER OF SEQ ID NOS: 8

<210> SEQ ID NO 1
<211> LENGTH: 3170
<212> TYPE: DNA
<213> ORGANISM: Mus musculus
<220> FEATURE:
<221> NAME/KEY: polyA_signal
<222> LOCATION: (3094)..(3099)
<220> FEATURE:
<223> OTHER INFORMATION: Coding sequence: (1)...(2172)

<400> SEQUENCE: 1
aaagggccgt cctggtccag ccgttccctg ggtgcccgtt gccggaactc tatcgcttcc      60
tgccctgagg aacaacccca tgtgggcaac tataggctgc taaggaccat cgggaagggc     120
aacttcgcca aagtcaagct ggctcggcat atcctcacgg gccgggaggt cgctattaag     180
atcattgata agacccagct gaaccccagt agcttgcaga agctgttcag agaagtccga     240
attatgaagg gactcaacca ccccaacatc gtgaagcttt ttgaggtgat agagacggag     300
aagacgctat acctggtgat ggaatacgct agcgcaggag aagtgtttga ctacctcgtg     360
tcgcacggcc gcatgaagga gaaggaggct cgagccaagt tgcggcagat cgtgtcagcc     420
gtgcactact gtcatcagaa gaacattgta cacagggatc taaaggctga aaacctgttg     480
ctggatgccg aggccaacat caaaatcgcc gacttcggct tcagcaatga gttcacgctg     540
ggctccaagc tggacacctt ctgtgggagc cccccatacg ccgccccaga gctgttccag     600
ggcaagaagt atgatgggcc agaggtggac atctggagcc tgggtgtcat cctgtacacg     660
ctggtcagcg gctccctgcc cttcgatggg cacaacctca aggagctgcg ggagcgaatc     720
ctcagaggaa agtaccgggt ccccttctac atgtctacag actgcgagag cattctgcgg     780
agatttctgg tgctgaaccc cgcaaaacgc tgtactctgg agcaaatcat gaaagacaaa     840
tggatcaaca tcggctatga gggtgaggag ctgaagccat acacggagcc tgaggaggac     900 ttcgggggaca ccaagagaat tgaggtgatg gtgggtatgg gctacacacg ggaagaaatc     960
aaagaggcct tgaccaacca gaagtacaac gaggtgaccg ccacctacct cctgctgggc    1020
aggaagactg atgagggtgg ggaccggggt gccccagggc tggccctggc acgggtgcgg    1080
gcgcccagcg acaccaccaa cgggacaagc tccagcaaag gcagcagcca caacaaaggg    1140
caacgggctt cttcctccac ctaccaccgc cagcgccgtc acagtgactt ctgtggcccg    1200
tcccctgccc cgctgcaccc gaagcgcacg ccaaccagca cgggagacac ggagctcaaa    1260
```

```
gaagagcgga tgccgggtcg gaaagcgagc tgcagtgcag tgggcagtgg aagtcgaggc    1320 ttgccccct  ccagcccat  ggtcagcagt gcccacaacc ccaataaggc agagatccct    1380
gagcggcgga aggacagcac tagcacccct aacaacctcc ccccagcat  gatgacccga    1440 agaaacacct atgtgtgcac agagcgacca ggatctgaac gcccgtcctt gttgccaaat    1500
ggcaaagaaa atagctccgg tacctcgcgg gtgcccctg  cctcgccttc cagtcatagc    1560
ctggctcccc cgtcaggcga gcggagccgc ctggctcggg gctccaccat ccgcagcacc    1620
ttccatgggg gccaggtccg agaccggcgg gcagggagcg ggagtggcgg gggtgtgcag    1680
aatggacccc cagcctcacc cacgcttgcc cacgaggccg caccctgcc  ctccgggcgg    1740 cctcgcccca ccaccaacct cttcaccaag ctgacctcca aactgacccg aagggtcaca    1800
gacgaacctg agagaatcgg gggacctgag gtcacaagtt gccatctacc ttgggataaa    1860
acggaaaccg cccccaggct gctccgattc ccctggagtg tgaagctgac cagctcgcga    1920
cctcctgagg ccctgatggc tgccatgcga caggccacag cggccgcccg ctgccggtgc    1980
cgccagccgc agccgttcct gctggcctgc ctgcacgggg gtgcgggcgg ccccgagccc    2040
ctgtcccatt tcgaagtgga ggtgtgccag ctgcccggc  ccggcctcag gggcgtcctc    2100
ttccgccgtg tggcgggcac cgccctggcc ttccgcaccc tcgtcacccg catctccaac    2160
gacctcgaac tctgagccac cgccaccact accaccgcca cagccaccat cacagcccgg    2220 gtccttctt  tctctggttc cttcacttc  cccaagaggg gaagaggaca gaggagaggg    2280
tgccctgtgt catgactgaa gtttccctgg attagattgg tggacagaga cagtgtgggg    2340
acacatgaca tgataagagg gctcagcagg gggagctggc accctcctag ggcctctggt    2400
gggacccccc tccccacaat cttgttcttc tgcagggcac ctgaggagac tttggggaca    2460
ggagtgagaa gggaaactga ggaaattctc ccattcaggg agagctgcca ggattaatga    2520
ctggagacag acttgggggg ttcagggagt tgggggagtc acagacagaa accttcccct    2580 cactcccct  tatgatcgaa cctccttcat gccccaggct ggcgcggggc actttgtaca    2640
aatccgtgta tatactcctg tccctctgca gaggtctctc ggggagctgc tgctgccgcc    2700
tccgattttt aagttattgc cccgcccctt ctgtcagctc ctcatctgca gcctgttact    2760
caataaacag taggagtccc tccaaccccg acctcctccc tggccgacct ggggtttccc    2820
ttctcagccc ttggcctgca ggtgagccag ggagctgggg acttgacccc aacctgtggt    2880
tctgcttgct gagcctttgt tatctcatct tcagaatggg aacagtgggg ttggaggatg    2940
ggtcaaggat gactatggaa gagggcagaa cagagctcag cctcttccac gaggcccag    3000 ccttctgtga caccctcctc ttggccactc actcccctct gccatattac actggaccca    3060
gagcctcttc ctattccagt aatacatgta ttcaataaac aatcaacgac tggtgccgac    3120
tccacgctag gcccagttct ggacataaaa aaaaaaaaa  aaaaaaaaa              3170
```

<210> SEQ ID NO 2
<211> LENGTH: 3250
<212> TYPE: DNA
<213> ORGANISM: Mus musculus
<220> FEATURE:
<221> NAME/KEY: polyA_signal
<222> LOCATION: (3174)..(3179)
<220> FEATURE:
<223> OTHER INFORMATION: Coding sequence: (1)...(1980)

<400> SEQUENCE: 2

```
aaagggccgt cctggtccag ccgttccctg ggtgcccgtt gccggaactc tatcgcttcc      60
```

```
tgccctgagg aacaacccca tgtgggcaac tataggctgc taaggaccat cgggaagggc        120
aacttcgcca aagtcaagct ggctcggcat atcctcacgg gccgggaggt cgctattaag        180
atcattgata agacccagct gaacccccagt agcttgcaga agctgttcag agaagtccga       240
attatgaagg gactcaacca ccccaacatc gtgaagcttt ttgaggtgat agagacggag        300
aagacgctat acctggtgat ggaatacgct agcgcaggag aagtgtttga ctacctcgtg        360
tcgcacggcc gcatgaagga aaggaggct cgagccaagt tgcggcagat cgtgtcagcc        420
gtgcactact gtcatcagaa gaacattgta cacagggatc taaaggctga aaacctgttg        480
ctggatgccg aggccaacat caaaatcgcc gacttcggct tcagcaatga gttcacgctg        540
ggctccaagc tggacacctt ctgtgggagc cccccatacg ccgccccaga gctgttccag        600
ggcaagaagt atgatgggcc agaggtggac atctggagcc tgggtgtcat cctgtacacg       660
ctggtcagcg gctccctgcc cttcgatggg cacaacctca aggagctgcg ggagcgaatc        720
ctcagaggaa agtaccgggt ccccttctac atgtctacag actgcgagag cattctgcgg        780
agatttctgg tgctgaaccc cgcaaaacgc tgtactctgg agcaaatcat gaaagacaaa        840
tggatcaaca tcggctatga gggtgaggag ctgaagccat acacggagcc tgaggaggac        900 ttcgggaca ccaagagaat tgaggtgatg gtgggtatgg gctacacacg ggaagaaatc        960
aaagaggcct tgaccaacca gaagtacaac gaggtgaccg ccacctacct cctgctgggc       1020
aggaagactg atgagggtgg ggaccggggt gccccagggc tggccctggc acgggtgcgg      1080
gcgcccagcg acaccaccaa cgggacaagc tccagcaaag gcagcagcca acaaaaggg      1140 caacgggctt cttcctccac ctaccaccgc cagcgccgtc acagtgactt ctgtggcccg        1200 tccctgccc cgctgcaccc gaagcgcagc ccaaccagca cgggagacac ggagctcaaa       1260
gaagagcgga tgccgggtcg gaaagcgagc tgcagtgcag tgggcagtgg aagtcgaggc       1320
ttgcccccct ccagcccat ggtcagcagt gcccacaacc ccaataaggc agagatccct       1380
gagcggcgga aggacagcac tagcacccct aacaacctcc cccccagcat gatgacccga      1440
agaaacacct atgtgtgcac agagcgacca ggatctgaac gcccgtcctt gttgccaaat       1500
ggcaaagaaa atagctccgg tacctcgcgg gtgcccctg cctcgccttc cagtcatagc        1560
ctggctcccc cgtcaggcga gcggagccgc ctggctcggg gctccaccat ccgcagcacc       1620
ttccatgggg gccaggtccg agaccggcgg gcagggagcg ggagtggcgg gggtgtgcag       1680
aatggacccc cagcctcacc cacgcttgcc cacgaggccg caccccctgcc ctccgggcgg      1740 cctcgcccca ccaccaacct cttcaccaag ctgacctcca aactgacccg aagggttacc       1800
ctcgatccct ctaaacggca gaactctaac cgctgtgtct cgggcgcctc tctgccccag       1860
ggatccaaaa tcaggtcaca gacgaacctg agagaatcgg gggacctgag gtcacaagtt       1920
gccatctacc ttgggataaa acggaaaccg cccccaggct gctccgattc ccctggagtg       1980
tgaagctgac cagctcgcga cctcctgagg ccctgatgcc tgccatgcga caggccacag      2040
cggccgcccg ctgccggtgc cgccagccgc agccgttcct gctggcctgc ctgcacgggg       2100 gtgcgggcg gcccgagccc ctgtcccatt tcgaagtgga ggtgtgccag ctgccccggc        2160
ccggcctcag gggcgtcctc ttccgccgtg tggcgggcac cgccctggcc ttccgcaccc       2220
tcgtcacccg catctccaac gacctcgaac tctgagccac cgccaccact accaccgcca      2280
cagccaccat cacagcccgg gtcccttctt tctctggttc cttcacttc cccaagaggg      2340 gaagaggaca gaggagaggg tgccctgtgt catgactgaa gtttccctgg attagattgg      2400
tggacagaga cagtgtgggg acacatgaca tgataagagg gctcagcagg gggagctggc        2460
```

-continued

```
acccteeetag ggcctctggt gggaccecce tcccecacaat cttgttettc tgcagggcac    2520 ctgaggagac tttggggaca ggagtgagaa gggaaactga ggaaattetc ccattcaggg    2580 agagctgcca ggattaatga ctggagacag acttgggggg ttcagggagt tgggggagtc    2640
acagacagaa accttcccct cactccccct tatgatcgaa cctccttcat gccccaggct    2700 ggcgcgggge actttgtaca aatccgtgta tatactcctg tccctctgca gaggtctctc    2760
ggggagctgc tgctgccgcc tccgattttt aagttattgc cccgccectt ctgtcagctc    2820 ctcatctgca gcctgttact caataaacag taggagtccc tccaaccccg acctcctccc    2880
tggccgacct ggggtttccc ttctcagccc ttggcctgca ggtgagccag ggagctgggg    2940
acttgacccc aacctgtggt tctgcttgct gagcctttgt tatctcatct tcagaatggg    3000
aacagtgggg ttggaggatg ggtcaaggat gactatggaa gagggcagaa cagagctcag    3060
cctcttccac gaggcccag ccttctgtga caccctcctc ttggccactc actcccctct    3120
gccatattac actggaccca gagcctcttc ctattccagt aatacatgta ttcaataaac    3180
aatcaacgac tggtgccgac tccacgctag gcccagttct ggacataaaa aaaaaaaaa    3240 aaaaaaaaaa                                                              3250
```

<210> SEQ ID NO 3
<211> LENGTH: 3312
<212> TYPE: DNA
<213> ORGANISM: Homo sapiens
<220> FEATURE:
<221> NAME/KEY: polyA_signal
<222> LOCATION: (3275)..(3280)
<220> FEATURE:
<223> OTHER INFORMATION: Coding sequence: (64)...(2319)

<400> SEQUENCE: 3

```
aggggaccct gggaccccg cccccccac ccggccgccc ctgccccccg ggacccggag      60
aagatgtctt cgcggacggt gctggccccg ggcaacgatc ggaactcgga cacgcatggc    120
accttgggca gtggccgctc ctcggacaaa ggcccgtcct ggtccagccg ctcactgggt    180
gcccgttgcc ggaactccat cgcctcctgt cccgaggagc agccccacgt gggcaactac    240
cgcctgctga ggaccattgg gaagggcaac tttgccaaag tcaagctggc tcggcacatc    300
ctcactggtc gggaggttgc catcaagatt atcgacaaaa cccagctgaa tcccagcagc    360
ctgcagaagc tgttccgaga agtccgcatc atgaagggcc taaaccaccc caacatcgtg    420
aagctctttg aggtgattga gactgagaag acgctgtacc tggtgatgga gtacgcaagt    480
gctggagaag tgtttgacta cctcgtgtcg catggccgca tgaaggagaa ggaagctcga    540
gccaagttcc gacagattgt ttcggctgtg cactattgtc accagaaaaa tattgtacac    600
agggacctga aggctgagaa cctcttgctg gatgccgagg ccaacatcaa gattgctgac    660
tttggcttca gcaacgagtt cacgctggga tcgaagctgg acgttctg cgggagcccc    720 ccatatgccg ccccggagct gtttcagggc aagaagtacg acgggccgga ggtggacatc    780
tggagcctgg gagtcatcct gtacacectc gtcagcggct ccctgccctt cgacgggcac    840
aacctcaagg agctgcggga gcgagtactc agagggaagt accgggtccc tttctacatg    900
tcaacagact gtgagagcat cctgcggaga ttttggtgc tgaacccagc taaacgctgt    960
actctcgagc aaatcatgaa agacaaatgg atcaacatcg ctatgagggt gaggagttg    1020 aagccataca cagagcccga ggaggacttc gggacacca agagaattga ggtgatggtg    1080
ggtatgggct acacacggga agaaatcaaa gagtccttga ccagccagaa gtacaacgaa    1140
```

-continued

```
gtgaccgcca cctacctcct gctgggcagg aagactgagg agggtgggga ccggggcgcc    1200
ccagggctgg ccctggcacg ggtgcgggcg cccagcgaca ccaccaacgg aacaagttcc    1260
agcaaaggca ccagccacag caaagggcag cggagttcct cttccaccta ccaccgccag    1320
cgcaggcata gcgatttctg tggcccatcc cctgcacccc tgcaccccaa acgcagcccg    1380
acgagcacgg ggaggcgga gctgaaggag agcggctgc caggccggaa ggcgagctgc      1440
agcaccgcgg ggagtgggag tcgagggctg cccccctcca gccccatggt cagcagcgcc    1500
cacaacccca acaaggcaga gatcccgagg cggcggaagg acagcacgag cacccccaac    1560
aacctccctc ctagcatgat gacccgcaga aacacctacg tttgcacaga acgcccgggg    1620
gctgagcgcc cgtcactgtt gccaaatggg aaagaaaaca gctcaggcac cccacgggtg    1680
cccctgcct ccccctccag tcacagcctg gcacccccat cagggagcg gagccgcctg      1740
gcacgtggtt ccaccatccg cagcaccttc catggtggcc aggtccggga ccggcgggca    1800
gggggtgggg gtggtggggg tgtgcagaat gggcccctg cctctcccac actggcccat     1860
gaggctgcac ccctgcccgc cgggcggccc cgccccacca ccaacctctt caccaagctg    1920
acctccaaac tgacccgaag ggtcgcagac gaacctgaga gaatcggggg acctgaggtc    1980
acaagttgcc atctaccttg ggatcaaacg gaaaccgccc ccggctgct ccgattcccc      2040
tggagtgtga agctgaccag ctcgcgccct cctgaggccc tgatggcagc tctgcgccag    2100
gccacagcag ccgcccgctg ccgctgccgc cagccacagc cgttcctgct ggcctgcctg    2160
cacggggtg cgggcgggcc cgagcccctg tcccacttcg aagtggaggt ctgccagctg     2220
ccccggccag gcttgcgggg agttctcttc cgccgtgtgg cgggcaccgc cctggccttc    2280
cgcaccctcg tcacccgcat ctccaacgac ctcgagctct gagccaccac ggtcccaggg   2340
cccttactct tcctctccct tgtcgccttc acttctacag gaggggaagg ggccagggag    2400
gggattctcc ctttatcatc acctcagttt ccctgaatta tatttggggg caaagattgt    2460
cccctctgct gttctctggg gccgctcagc acagaagaag gatgagggg ctcagcgggg     2520
ggagctggca ccttcctgga gcctccagcc agtcctgtcc tccctcgccc taccaagagg   2580
gcacctgagg agactttggg gacagggcag gggcagggag ggaaactgag gaaatcttcc    2640
attcctccca acagctcaaa attaggcctt gggcaggggc agggagagct gctgagccta    2700
aagactggag aatctggggg actgggagtg ggggtcagag aggcagattc cttcccctcc    2760
cgtccctca cgctcaaacc cccacttcct gccccaggct ggcgcgggc actttgtaca      2820
aatccttgta aataccccac accctcccct ctgcaaaggt ctcttgagga gctgccgctg    2880
tcacctacgg tttttaagtt attacacccc gaccctcctc ctgtcagccc cctcacctgc    2940
agcctgttgc ccaataaatt taggagagtc cccccctccc caatgctgac cctaggattt    3000
tccttccctg ccctcacctg caaatgagtt aaagaagagg cgtgggaatc caggcagtgg    3060
tttttccttt cggagcctcg gttttctcat ctgcagaatg ggagcggtgg gggtgggaag    3120
gtaaggatgg tcgtggaaga aggcaggatg gaactcggcc tcatcccga ggccccagtt     3180
cctatatcgg gccccccatt catccactca cactcccagc caccatgtta cactggactc    3240
taagccactt cttactccag tagtaaattt attcaataaa caatcattga cccatgccta    3300
aaaaaaaaaa aa                                                        3312
```

<210> SEQ ID NO 4
<211> LENGTH: 3392
<212> TYPE: DNA

<213> ORGANISM: Homo sapiens
<220> FEATURE:
<221> NAME/KEY: polyA_signal
<222> LOCATION: (3355)..(3360)
<220> FEATURE:
<223> OTHER INFORMATION: Coding sequence: (64)...(2127)

<400> SEQUENCE: 4

```
aggggaccct gggaccccg cccccccac ccggccgccc ctgcccccg ggacccggag     60
aagatgtctt cgcggacggt gctggccccg ggcaacgatc ggaactcgga cacgcatggc    120
accttgggca gtggccgctc ctcggacaaa ggcccgtcct ggtccagccg ctcactgggt    180
gcccgttgcc ggaactccat cgcctcctgt cccgaggagc agccccacgt gggcaactac    240
cgcctgctga ggaccattgg gaagggcaac tttgccaaag tcaagctggc tcggacatc    300
ctcactggtc gggaggttgc catcaagatt atcgacaaaa cccagctgaa tcccagcagc    360
ctgcagaagc tgttccgaga gtccgcatc atgaagggcc taaaccaccc caacatcgtg    420
aagctctttg aggtgattga gactgagaag acgctgtacc tggtgatgga gtacgcaagt    480
gctggagaag tgtttgacta cctcgtgtcg catggccgca tgaaggagaa ggaagctcga    540
gccaagttcc gacagattgt tcggctgtg cactattgtc accagaaaaa tattgtacac    600
agggacctga aggctgagaa cctcttgctg gatgccgagg ccaacatcaa gattgctgac    660
tttggcttca gcaacgagtt cacgctggga tcgaagctgg acacgttctg cgggagcccc    720
ccatatgccg ccccggagct gtttcagggc aagaagtacg acgggccgga ggtggacatc    780
tggagcctgg gagtcatcct gtacaccctc gtcagcggct ccctgccctt cgacgggcac    840
aacctcaagg agctgcggga gcgagtactc agagggaagt accgggtccc tttctacatg    900
tcaacagact gtgagagcat cctgcggaga ttttggtgc tgaacccagc taaacgctgt    960
actctcgagc aaatcatgaa agacaaatgg atcaacatcg ctatgaggg tgaggagttg   1020
aagccatca cagagcccga ggaggacttc ggggacacca agagaattga ggtgatggtg   1080
ggtatgggct acacacggga agaaatcaaa gagtccttga ccagccagaa gtacaacgaa   1140
gtgaccgcca cctacctcct gctgggcagg aagactgagg agggtgggga ccggggcgcc   1200
ccagggctgg ccctggcacg ggtgcgggcg cccagcgaca ccaccaacgg aacaagttcc   1260
agcaaaggca ccagccacag caaagggcag cggagttcct cttccaccta ccaccgccag   1320
cgcaggcata gcgatttctg tggcccatcc cctgcacccc tgcaccccaa acgcagcccg   1380
acgagcacgg gggaggcgga gctgaaggag gagcggctgc caggccggaa ggcgagctgc   1440
agcaccgcgg ggagtgggag tcgagggctg cccccctcca gccccatggt cagcagcgcc   1500
cacaacccca acaaggcaga gatcccgag cggcggaagg acagcacgag caccccaac   1560
aacctccctc ctagcatgat gacccgcaga aacacctacg tttgcacaga acgcccgggg   1620
gctgagcgcc cgtcactgtt gccaaatggg aaagaaaaca gctcaggcac ccacgggtg   1680
ccccctgcct cccctccag tcacagcctg gcacccccat caggggagcg gagccgcctg   1740
gcacgtggtt ccaccatccg cagcaccttc catggtggcc aggtccggga ccggcgggca   1800
gggggtgggg gtggtggggg tgtgcagaat gggccccctg cctctcccac actggcccat   1860
gaggctgcac ccctgcccgc cgggcggccc cgccccacca ccaacctctt caccaagctg   1920
acctccaaac tgacccgaag ggttaccctc gatccctcta acggcagaa ctctaaccgc   1980
tgtgtttcgg gcgcctctct gccccaggga tccaagatca ggtcgcagac gaacctgaga   2040
gaatcggggg acctgaggtc acaagttgcc atctaccttg ggatcaaacg gaaaccgccc   2100
```

```
cccggctgct ccgattcccc tggagtgtga agctgaccag ctcgcgccct cctgaggccc    2160
tgatggcagc tctgcgccag ccacagcag ccgcccgctg ccgctgccgc cagccacagc    2220
cgttcctgct ggcctgcctg cacggggtg cgggcgggcc cgagcccctg tcccacttcg    2280
aagtggaggt ctgccagctg ccccggccag gcttgcgggg agttctcttc cgccgtgtgg    2340
cgggcaccgc cctggccttc cgcaccctcg tcacccgcat ctccaacgac ctcgagctct    2400
gagccaccac ggtcccaggg cccttactct tcctctccct tgtcgccttc acttctacag    2460
gaggggaagg ggccagggag gggattctcc ctttatcatc acctcagttt ccctgaatta    2520
tatttggggg caaagattgt cccctctgct gttctctggg gccgctcagc acagaagaag    2580
gatgaggggg ctcagcgggg ggagctggca ccttcctgga gcctccagcc agtcctgtcc    2640
tccctcgccc taccaagagg gcacctgagg agactttggg gacagggcag gggcagggag    2700
ggaaactgag gaaatcttcc attcctccca acagctcaaa attaggcctt gggcaggggc    2760
agggagagct gctgagccta aagactggag aatctggggg actgggagtg ggggtcagag    2820
aggcagattc cttcccctcc cgtcccctca cgctcaaacc cccacttcct gccccaggct    2880
ggcgcggggc actttgtaca aatccttgta aataccccac accctcccct ctgcaaaggt    2940
ctcttgagga gctgccgctg tcacctacgg ttttaagtt attacacccc gaccctcctc    3000
ctgtcagccc cctcacctgc agcctgttgc ccaataaatt taggagagtc cccccctccc    3060
caatgctgac cctaggattt tccttccctg ccctcacctg caaatgagtt aaagaagagg    3120
cgtgggaatc caggcagtgg ttttcctttt cggagcctcg gttttctcat ctgcagaatg    3180
ggagcggtgg gggtgggaag gtaaggatgg tcgtggaaga aggcaggatg gaactcggcc    3240
tcatccccga ggccccagtt cctatatcgg gcccccatt catccactca cactcccagc    3300
caccatgtta cactggactc taagccactt cttactccag tagtaaattt attcaataaa    3360
caatcattga cccatgccta aaaaaaaaaa aa                                 3392
```

<210> SEQ ID NO 5
<211> LENGTH: 724
<212> TYPE: PRT
<213> ORGANISM: Mus musculus

<400> SEQUENCE: 5

```
Lys Gly Pro Ser Trp Ser Ser Arg Ser Leu Gly Ala Arg Cys Arg Asn
  1               5                  10                  15

Ser Ile Ala Ser Cys Pro Glu Glu Gln Pro His Val Gly Asn Tyr Arg
             20                  25                  30

Leu Leu Arg Thr Ile Gly Lys Gly Asn Phe Ala Lys Val Lys Leu Ala
         35                  40                  45

Arg His Ile Leu Thr Gly Arg Glu Val Ala Ile Lys Ile Ile Asp Lys
     50                  55                  60

Thr Gln Leu Asn Pro Ser Ser Leu Gln Lys Leu Phe Arg Glu Val Arg
 65                  70                  75                  80

Ile Met Lys Gly Leu Asn His Pro Asn Ile Val Lys Leu Phe Glu Val
                 85                  90                  95

Ile Glu Thr Glu Lys Thr Leu Tyr Leu Val Met Glu Tyr Ala Ser Ala
            100                 105                 110

Gly Glu Val Phe Asp Tyr Leu Val Ser His Gly Arg Met Lys Glu Lys
        115                 120                 125

Glu Ala Arg Ala Lys Leu Arg Gln Ile Val Ser Ala Val His Tyr Cys
    130                 135                 140
```

```
His Gln Lys Asn Ile Val His Arg Asp Leu Lys Ala Glu Asn Leu Leu
145                 150                 155                 160

Leu Asp Ala Glu Ala Asn Ile Lys Ile Ala Asp Phe Gly Phe Ser Asn
            165                 170                 175

Glu Phe Thr Leu Gly Ser Lys Leu Asp Thr Phe Cys Gly Ser Pro Pro
        180                 185                 190

Tyr Ala Ala Pro Glu Leu Phe Gln Gly Lys Lys Tyr Asp Gly Pro Glu
    195                 200                 205

Val Asp Ile Trp Ser Leu Gly Val Ile Leu Tyr Thr Leu Val Ser Gly
210                 215                 220

Ser Leu Pro Phe Asp Gly His Asn Leu Lys Glu Leu Arg Glu Arg Ile
225                 230                 235                 240

Leu Arg Gly Lys Tyr Arg Val Pro Phe Tyr Met Ser Thr Asp Cys Glu
                245                 250                 255

Ser Ile Leu Arg Arg Phe Leu Val Leu Asn Pro Ala Lys Arg Cys Thr
            260                 265                 270

Leu Glu Gln Ile Met Lys Asp Lys Trp Ile Asn Ile Gly Tyr Glu Gly
        275                 280                 285

Glu Glu Leu Lys Pro Tyr Thr Glu Pro Glu Glu Asp Phe Gly Asp Thr
290                 295                 300

Lys Arg Ile Glu Val Met Val Gly Met Gly Tyr Thr Arg Glu Glu Ile
305                 310                 315                 320

Lys Glu Ala Leu Thr Asn Gln Lys Tyr Asn Glu Val Thr Ala Thr Tyr
                325                 330                 335

Leu Leu Leu Gly Arg Lys Thr Asp Glu Gly Gly Asp Arg Gly Ala Pro
            340                 345                 350

Gly Leu Ala Leu Ala Arg Val Arg Ala Pro Ser Asp Thr Thr Asn Gly
        355                 360                 365

Thr Ser Ser Ser Lys Gly Ser Ser His Asn Lys Gly Gln Arg Ala Ser
    370                 375                 380

Ser Ser Thr Tyr His Arg Gln Arg Arg His Ser Asp Phe Cys Gly Pro
385                 390                 395                 400

Ser Pro Ala Pro Leu His Pro Lys Arg Thr Pro Thr Ser Thr Gly Asp
                405                 410                 415

Thr Glu Leu Lys Glu Glu Arg Met Pro Gly Arg Lys Ala Ser Cys Ser
            420                 425                 430

Ala Val Gly Ser Gly Ser Arg Gly Leu Pro Pro Ser Ser Pro Met Val
        435                 440                 445

Ser Ser Ala His Asn Pro Asn Lys Ala Glu Ile Pro Glu Arg Arg Lys
    450                 455                 460

Asp Ser Thr Ser Thr Pro Asn Asn Leu Pro Pro Ser Met Met Thr Arg
465                 470                 475                 480

Arg Asn Thr Tyr Val Cys Thr Glu Arg Pro Gly Ser Glu Arg Pro Ser
                485                 490                 495

Leu Leu Pro Asn Gly Lys Glu Asn Ser Ser Gly Thr Ser Arg Val Pro
            500                 505                 510

Pro Ala Ser Pro Ser Ser His Ser Leu Ala Pro Pro Ser Gly Glu Arg
        515                 520                 525

Ser Arg Leu Ala Arg Gly Ser Thr Ile Arg Ser Thr Phe His Gly Gly
    530                 535                 540

Gln Val Arg Asp Arg Arg Ala Gly Ser Gly Ser Gly Gly Gly Val Gln
545                 550                 555                 560

Asn Gly Pro Pro Ala Ser Pro Thr Leu Ala His Glu Ala Ala Pro Leu
```

-continued

```
                    565                 570                 575
Pro Ser Gly Arg Pro Arg Pro Thr Thr Asn Leu Phe Thr Lys Leu Thr
                580                 585                 590

Ser Lys Leu Thr Arg Arg Val Thr Asp Glu Pro Glu Arg Ile Gly Gly
            595                 600                 605

Pro Glu Val Thr Ser Cys His Leu Pro Trp Asp Lys Thr Glu Thr Ala
        610                 615                 620

Pro Arg Leu Leu Arg Phe Pro Trp Ser Val Lys Leu Thr Ser Ser Arg
625                 630                 635                 640

Pro Pro Glu Ala Leu Met Ala Ala Met Arg Gln Ala Thr Ala Ala Ala
                645                 650                 655

Arg Cys Arg Cys Arg Gln Pro Gln Pro Phe Leu Leu Ala Cys Leu His
            660                 665                 670

Gly Gly Ala Gly Gly Pro Glu Pro Leu Ser His Phe Glu Val Glu Val
        675                 680                 685

Cys Gln Leu Pro Arg Pro Gly Leu Arg Gly Val Leu Phe Arg Arg Val
    690                 695                 700

Ala Gly Thr Ala Leu Ala Phe Arg Thr Leu Val Thr Arg Ile Ser Asn
705                 710                 715                 720

Asp Leu Glu Leu

<210> SEQ ID NO 6
<211> LENGTH: 660
<212> TYPE: PRT
<213> ORGANISM: Mus musculus

<400> SEQUENCE: 6

Lys Gly Pro Ser Trp Ser Ser Arg Ser Leu Gly Ala Arg Cys Arg Asn
  1               5                  10                  15

Ser Ile Ala Ser Cys Pro Glu Glu Gln Pro His Val Gly Asn Tyr Arg
            20                  25                  30

Leu Leu Arg Thr Ile Gly Lys Gly Asn Phe Ala Lys Val Lys Leu Ala
        35                  40                  45

Arg His Ile Leu Thr Gly Arg Glu Val Ala Ile Lys Ile Ile Asp Lys
    50                  55                  60

Thr Gln Leu Asn Pro Ser Ser Leu Gln Lys Leu Phe Arg Glu Val Arg
65                  70                  75                  80

Ile Met Lys Gly Leu Asn His Pro Asn Ile Val Lys Leu Phe Glu Val
                85                  90                  95

Ile Glu Thr Glu Lys Thr Leu Tyr Leu Val Met Glu Tyr Ala Ser Ala
            100                 105                 110

Gly Glu Val Phe Asp Tyr Leu Val Ser His Gly Arg Met Lys Glu Lys
        115                 120                 125

Glu Ala Arg Ala Lys Leu Arg Gln Ile Val Ser Ala Val His Tyr Cys
    130                 135                 140

His Gln Lys Asn Ile Val His Arg Asp Leu Lys Ala Glu Asn Leu Leu
145                 150                 155                 160

Leu Asp Ala Glu Ala Asn Ile Lys Ile Ala Asp Phe Gly Phe Ser Asn
                165                 170                 175

Glu Phe Thr Leu Gly Ser Lys Leu Asp Thr Phe Cys Gly Ser Pro Pro
            180                 185                 190

Tyr Ala Ala Pro Glu Leu Phe Gln Gly Lys Lys Tyr Asp Gly Pro Glu
        195                 200                 205

Val Asp Ile Trp Ser Leu Gly Val Ile Leu Tyr Thr Leu Val Ser Gly
```

-continued

```
            210                 215                 220
Ser Leu Pro Phe Asp Gly His Asn Leu Lys Glu Leu Arg Glu Arg Ile
225                 230                 235                 240

Leu Arg Gly Lys Tyr Arg Val Pro Phe Tyr Met Ser Thr Asp Cys Glu
                245                 250                 255

Ser Ile Leu Arg Arg Phe Leu Val Leu Asn Pro Ala Lys Arg Cys Thr
                260                 265                 270

Leu Glu Gln Ile Met Lys Asp Lys Trp Ile Asn Ile Gly Tyr Glu Gly
                275                 280                 285

Glu Glu Leu Lys Pro Tyr Thr Glu Pro Glu Glu Asp Phe Gly Asp Thr
290                 295                 300

Lys Arg Ile Glu Val Met Val Gly Met Gly Tyr Thr Arg Glu Glu Ile
305                 310                 315                 320

Lys Glu Ala Leu Thr Asn Gln Lys Tyr Asn Glu Val Thr Ala Thr Tyr
                325                 330                 335

Leu Leu Leu Gly Arg Lys Thr Asp Glu Gly Gly Asp Arg Gly Ala Pro
                340                 345                 350

Gly Leu Ala Leu Ala Arg Val Arg Ala Pro Ser Asp Thr Thr Asn Gly
                355                 360                 365

Thr Ser Ser Ser Lys Gly Ser Ser His Asn Lys Gly Gln Arg Ala Ser
370                 375                 380

Ser Ser Thr Tyr His Arg Gln Arg His Ser Asp Phe Cys Gly Pro
385                 390                 395                 400

Ser Pro Ala Pro Leu His Pro Lys Arg Ser Pro Thr Thr Gly Asp
                405                 410                 415

Thr Glu Leu Lys Glu Glu Arg Met Pro Gly Arg Lys Ala Ser Cys Ser
                420                 425                 430

Ala Val Gly Ser Gly Ser Arg Gly Leu Pro Pro Ser Ser Pro Met Val
                435                 440                 445

Ser Ser Ala His Asn Pro Asn Lys Ala Glu Ile Pro Glu Arg Arg Lys
                450                 455                 460

Asp Ser Thr Ser Thr Pro Asn Asn Leu Pro Pro Ser Met Met Thr Arg
465                 470                 475                 480

Arg Asn Thr Tyr Val Cys Thr Glu Arg Pro Gly Ser Glu Arg Pro Ser
                485                 490                 495

Leu Leu Pro Asn Gly Lys Glu Asn Ser Ser Gly Thr Ser Arg Val Pro
                500                 505                 510

Pro Ala Ser Pro Ser Ser His Ser Leu Ala Pro Ser Gly Glu Arg
                515                 520                 525

Ser Arg Leu Ala Arg Gly Ser Thr Ile Arg Ser Thr Phe His Gly Gly
                530                 535                 540

Gln Val Arg Asp Arg Arg Ala Gly Ser Gly Ser Gly Gly Val Gln
545                 550                 555                 560

Asn Gly Pro Pro Ala Ser Pro Thr Leu Ala His Glu Ala Ala Pro Leu
                565                 570                 575

Pro Ser Gly Arg Pro Arg Pro Thr Thr Asn Leu Phe Thr Lys Leu Thr
                580                 585                 590

Ser Lys Leu Thr Arg Arg Val Thr Leu Asp Pro Ser Lys Arg Gln Asn
                595                 600                 605

Ser Asn Arg Cys Val Ser Gly Ala Ser Leu Pro Gln Gly Ser Lys Ile
                610                 615                 620

Arg Ser Gln Thr Asn Leu Arg Glu Ser Gly Asp Leu Arg Ser Gln Val
625                 630                 635                 640
```

Ala Ile Tyr Leu Gly Ile Lys Arg Lys Pro Pro Gly Cys Ser Asp
                645                 650                 655

Ser Pro Gly Val
            660

<210> SEQ ID NO 7
<211> LENGTH: 752
<212> TYPE: PRT
<213> ORGANISM: Homo sapiens

<400> SEQUENCE: 7

Met Ser Ser Arg Thr Val Leu Ala Pro Gly Asn Asp Arg Asn Ser Asp
 1               5                  10                  15

Thr His Gly Thr Leu Gly Ser Gly Arg Ser Ser Asp Lys Gly Pro Ser
             20                  25                  30

Trp Ser Arg Ser Leu Gly Ala Arg Cys Arg Asn Ser Ile Ala Ser
         35                  40                  45

Cys Pro Glu Glu Gln Pro His Val Gly Asn Tyr Arg Leu Leu Arg Thr
     50                  55                  60

Ile Gly Lys Gly Asn Phe Ala Lys Val Lys Leu Ala Arg His Ile Leu
 65                  70                  75                  80

Thr Gly Arg Glu Val Ala Ile Lys Ile Ile Asp Lys Thr Gln Leu Asn
                 85                  90                  95

Pro Ser Ser Leu Gln Lys Leu Phe Arg Glu Val Arg Ile Met Lys Gly
            100                 105                 110

Leu Asn His Pro Asn Ile Val Lys Leu Phe Glu Val Ile Glu Thr Glu
        115                 120                 125

Lys Thr Leu Tyr Leu Val Met Glu Tyr Ala Ser Ala Gly Glu Val Phe
    130                 135                 140

Asp Tyr Leu Val Ser His Gly Arg Met Lys Glu Lys Glu Ala Arg Ala
145                 150                 155                 160

Lys Phe Arg Gln Ile Val Ser Ala Val His Tyr Cys His Gln Lys Asn
                165                 170                 175

Ile Val His Arg Asp Leu Lys Ala Glu Asn Leu Leu Leu Asp Ala Glu
            180                 185                 190

Ala Asn Ile Lys Ile Ala Asp Phe Gly Phe Ser Asn Glu Phe Thr Leu
        195                 200                 205

Gly Ser Lys Leu Asp Thr Phe Cys Gly Ser Pro Pro Tyr Ala Ala Pro
    210                 215                 220

Glu Leu Phe Gln Gly Lys Lys Tyr Asp Gly Pro Glu Val Asp Ile Trp
225                 230                 235                 240

Ser Leu Gly Val Ile Leu Tyr Thr Leu Val Ser Gly Ser Leu Pro Phe
                245                 250                 255

Asp Gly His Asn Leu Lys Glu Leu Arg Glu Arg Val Leu Arg Gly Lys
            260                 265                 270

Tyr Arg Val Pro Phe Tyr Met Ser Thr Asp Cys Glu Ser Ile Leu Arg
        275                 280                 285

Arg Phe Leu Val Leu Asn Pro Ala Lys Arg Cys Thr Leu Glu Gln Ile
    290                 295                 300

Met Lys Asp Lys Trp Ile Asn Ile Gly Tyr Glu Gly Glu Glu Leu Lys
305                 310                 315                 320

Pro Tyr Thr Glu Pro Glu Glu Asp Phe Gly Asp Thr Lys Arg Ile Glu
                325                 330                 335

Val Met Val Gly Met Gly Tyr Thr Arg Glu Glu Ile Lys Glu Ser Leu

-continued

```
                340                 345                 350
Thr Ser Gln Lys Tyr Asn Glu Val Thr Ala Thr Tyr Leu Leu Gly
            355                 360                 365

Arg Lys Thr Glu Glu Gly Gly Asp Arg Gly Ala Pro Gly Leu Ala Leu
    370                 375                 380

Ala Arg Val Arg Ala Pro Ser Asp Thr Thr Asn Gly Thr Ser Ser Ser
385                 390                 395                 400

Lys Gly Thr Ser His Ser Lys Gly Gln Arg Ser Ser Ser Thr Tyr
            405                 410                 415

His Arg Gln Arg Arg His Ser Asp Phe Cys Gly Pro Ser Pro Ala Pro
            420                 425                 430

Leu His Pro Lys Arg Ser Pro Thr Ser Thr Gly Glu Ala Glu Leu Lys
            435                 440                 445

Glu Glu Arg Leu Pro Gly Arg Lys Ala Ser Cys Ser Thr Ala Gly Ser
    450                 455                 460

Gly Ser Arg Gly Leu Pro Ser Ser Pro Met Val Ser Ser Ala His
465                 470                 475                 480

Asn Pro Asn Lys Ala Glu Ile Pro Glu Arg Arg Lys Asp Ser Thr Ser
            485                 490                 495

Thr Pro Asn Asn Leu Pro Pro Ser Met Met Thr Arg Arg Asn Thr Tyr
            500                 505                 510

Val Cys Thr Glu Arg Pro Gly Ala Glu Arg Pro Ser Leu Leu Pro Asn
    515                 520                 525

Gly Lys Glu Asn Ser Ser Gly Thr Pro Arg Val Pro Pro Ala Ser Pro
            530                 535                 540

Ser Ser His Ser Leu Ala Pro Pro Ser Gly Glu Arg Ser Arg Leu Ala
545                 550                 555                 560

Arg Gly Ser Thr Ile Arg Ser Thr Phe His Gly Gly Gln Val Arg Asp
            565                 570                 575

Arg Arg Ala Gly Gly Gly Gly Gly Gly Val Gln Asn Gly Pro Pro
            580                 585                 590

Ala Ser Pro Thr Leu Ala His Glu Ala Ala Pro Leu Pro Ala Gly Arg
            595                 600                 605

Pro Arg Pro Thr Thr Asn Leu Phe Thr Lys Leu Thr Ser Lys Leu Thr
    610                 615                 620

Arg Arg Val Ala Asp Glu Pro Glu Arg Ile Gly Gly Pro Glu Val Thr
625                 630                 635                 640

Ser Cys His Leu Pro Trp Asp Gln Thr Glu Thr Ala Pro Arg Leu Leu
            645                 650                 655

Arg Phe Pro Trp Ser Val Lys Leu Thr Ser Ser Arg Pro Pro Glu Ala
            660                 665                 670

Leu Met Ala Ala Leu Arg Gln Ala Thr Ala Ala Ala Arg Cys Arg Cys
            675                 680                 685

Arg Gln Pro Gln Pro Phe Leu Leu Ala Cys Leu His Gly Gly Ala Gly
    690                 695                 700

Gly Pro Glu Pro Leu Ser His Phe Glu Val Glu Val Cys Gln Leu Pro
705                 710                 715                 720

Arg Pro Gly Leu Arg Gly Val Leu Phe Arg Arg Val Ala Gly Thr Ala
            725                 730                 735

Leu Ala Phe Arg Thr Leu Val Thr Arg Ile Ser Asn Asp Leu Glu Leu
            740                 745                 750
```

<210> SEQ ID NO 8

```
<211> LENGTH: 688
<212> TYPE: PRT
<213> ORGANISM: Homo sapiens

<400> SEQUENCE: 8

Met Ser Ser Arg Thr Val Leu Ala Pro Gly Asn Asp Arg Asn Ser Asp
 1               5                  10                  15

Thr His Gly Thr Leu Gly Ser Gly Arg Ser Ser Asp Lys Gly Pro Ser
             20                  25                  30

Trp Ser Arg Ser Leu Gly Ala Arg Cys Arg Asn Ser Ile Ala Ser
         35                  40                  45

Cys Pro Glu Glu Gln Pro His Val Gly Asn Tyr Arg Leu Leu Arg Thr
     50                  55                  60

Ile Gly Lys Gly Asn Phe Ala Lys Val Lys Leu Ala Arg His Ile Leu
 65                  70                  75                  80

Thr Gly Arg Glu Val Ala Ile Lys Ile Ile Asp Lys Thr Gln Leu Asn
             85                  90                  95

Pro Ser Ser Leu Gln Lys Leu Phe Arg Glu Val Arg Ile Met Lys Gly
            100                 105                 110

Leu Asn His Pro Asn Ile Val Lys Leu Phe Glu Val Ile Glu Thr Glu
            115                 120                 125

Lys Thr Leu Tyr Leu Val Met Glu Tyr Ala Ser Ala Gly Glu Val Phe
130                 135                 140

Asp Tyr Leu Val Ser His Gly Arg Met Lys Glu Lys Glu Ala Arg Ala
145                 150                 155                 160

Lys Phe Arg Gln Ile Val Ser Ala Val His Tyr Cys His Gln Lys Asn
                165                 170                 175

Ile Val His Arg Asp Leu Lys Ala Glu Asn Leu Leu Leu Asp Ala Glu
            180                 185                 190

Ala Asn Ile Lys Ile Ala Asp Phe Gly Phe Ser Asn Glu Phe Thr Leu
            195                 200                 205

Gly Ser Lys Leu Asp Thr Phe Cys Gly Ser Pro Pro Tyr Ala Ala Pro
    210                 215                 220

Glu Leu Phe Gln Gly Lys Lys Tyr Asp Gly Pro Glu Val Asp Ile Trp
225                 230                 235                 240

Ser Leu Gly Val Ile Leu Tyr Thr Leu Val Ser Gly Ser Leu Pro Phe
                245                 250                 255

Asp Gly His Asn Leu Lys Glu Leu Arg Glu Arg Val Leu Arg Gly Lys
            260                 265                 270

Tyr Arg Val Pro Phe Tyr Met Ser Thr Asp Cys Glu Ser Ile Leu Arg
        275                 280                 285

Arg Phe Leu Val Leu Asn Pro Ala Lys Arg Cys Thr Leu Glu Gln Ile
290                 295                 300

Met Lys Asp Lys Trp Ile Asn Ile Gly Tyr Glu Gly Glu Glu Leu Lys
305                 310                 315                 320

Pro Tyr Thr Glu Pro Glu Glu Asp Phe Gly Asp Thr Lys Arg Ile Glu
                325                 330                 335

Val Met Val Gly Met Gly Tyr Thr Arg Glu Glu Ile Lys Glu Ser Leu
            340                 345                 350

Thr Ser Gln Lys Tyr Asn Glu Val Thr Ala Thr Tyr Leu Leu Leu Gly
        355                 360                 365

Arg Lys Thr Glu Glu Gly Gly Asp Arg Gly Ala Pro Gly Leu Ala Leu
    370                 375                 380

Ala Arg Val Arg Ala Pro Ser Asp Thr Thr Asn Gly Thr Ser Ser Ser
```

-continued

```
385                 390                 395                 400
Lys Gly Thr Ser His Ser Lys Gly Gln Arg Ser Ser Ser Thr Tyr
                405                 410                 415
His Arg Gln Arg Arg His Ser Asp Phe Cys Gly Pro Ser Pro Ala Pro
            420                 425                 430
Leu His Pro Lys Arg Ser Pro Thr Ser Thr Gly Glu Ala Glu Leu Lys
            435                 440                 445
Glu Glu Arg Leu Pro Gly Arg Lys Ala Ser Cys Ser Thr Ala Gly Ser
        450                 455                 460
Gly Ser Arg Gly Leu Pro Pro Ser Ser Pro Met Val Ser Ser Ala His
465                 470                 475                 480
Asn Pro Asn Lys Ala Glu Ile Pro Glu Arg Arg Lys Asp Ser Thr Ser
            485                 490                 495
Thr Pro Asn Asn Leu Pro Pro Ser Met Met Thr Arg Arg Asn Thr Tyr
            500                 505                 510
Val Cys Thr Glu Arg Pro Gly Ala Glu Arg Pro Ser Leu Leu Pro Asn
            515                 520                 525
Gly Lys Glu Asn Ser Ser Gly Thr Pro Arg Val Pro Pro Ala Ser Pro
    530                 535                 540
Ser Ser His Ser Leu Ala Pro Pro Ser Gly Glu Arg Ser Arg Leu Ala
545                 550                 555                 560
Arg Gly Ser Thr Ile Arg Ser Thr Phe His Gly Gly Gln Val Arg Asp
                565                 570                 575
Arg Arg Ala Gly Gly Gly Gly Gly Val Gln Asn Gly Pro Pro
            580                 585                 590
Ala Ser Pro Thr Leu Ala His Glu Ala Ala Pro Leu Pro Ala Gly Arg
        595                 600                 605
Pro Arg Pro Thr Thr Asn Leu Phe Thr Lys Leu Thr Ser Lys Leu Thr
    610                 615                 620
Arg Arg Val Thr Leu Asp Pro Ser Lys Arg Gln Asn Ser Asn Arg Cys
625                 630                 635                 640
Val Ser Gly Ala Ser Leu Pro Gln Gly Ser Lys Ile Arg Ser Gln Thr
                645                 650                 655
Asn Leu Arg Glu Ser Gly Asp Leu Arg Ser Gln Val Ala Ile Tyr Leu
            660                 665                 670
Gly Ile Lys Arg Lys Pro Pro Gly Cys Ser Asp Ser Pro Gly Val
            675                 680                 685
```